US012599327B2

(12) United States Patent
Wang et al.

(10) Patent No.: US 12,599,327 B2
(45) Date of Patent: Apr. 14, 2026

(54) MEASUREMENT STATION WITH ELECTROCARDIOGRAM MEASUREMENT

(71) Applicant: Withings, Issy les Moulineaux (FR)

(72) Inventors: Jean-Louis Wang, Issy les Moulineaux (FR); Antoine Merlot, Issy les Moulineaux (FR)

(73) Assignee: Withings, Issy les Moulineaux (FR)

( * ) Notice: Subject to any disclaimer, the term of this patent is extended or adjusted under 35 U.S.C. 154(b) by 602 days.

(21) Appl. No.: 18/087,401

(22) Filed: Dec. 22, 2022

(65) Prior Publication Data

US 2023/0210430 A1 Jul. 6, 2023

(30) Foreign Application Priority Data

Dec. 31, 2021 (FR) ....................................... 2114744

(51) Int. Cl.
| | |
|---|---|
| *A61B 5/26* | (2021.01) |
| *A61B 5/00* | (2006.01) |
| *A61B 5/0535* | (2021.01) |
| *A61B 5/282* | (2021.01) |
| *A61B 5/305* | (2021.01) |
| *A61B 5/346* | (2021.01) |

(52) U.S. Cl.
CPC ................ *A61B 5/26* (2021.01); *A61B 5/282* (2021.01); *A61B 5/346* (2021.01); *A61B 5/702* (2013.01); *A61B 2562/0209* (2013.01)

(58) Field of Classification Search
CPC ........... A61B 5/282; A61B 5/30; A61B 5/305; A61B 5/6892; A61B 5/6896; A61B 5/6898; A61B 5/702
See application file for complete search history.

(56) References Cited

U.S. PATENT DOCUMENTS

| | | | |
|---|---|---|---|
| 5,792,063 A | 8/1998 | Danielsson et al. | |
| 2016/0287128 A1 | 10/2016 | Jain et al. | |
| 2017/0188951 A1* | 7/2017 | Banet | A61B 5/0261 |
| 2021/0212587 A1* | 7/2021 | Warner | A61B 5/305 |

FOREIGN PATENT DOCUMENTS

| | | | | |
|---|---|---|---|---|
| CN | 116801792 A * | 9/2023 | ........... | A61B 5/0205 |
| EP | 2 737 847 A2 | 6/2014 | | |
| EP | 3 087 914 A1 | 11/2016 | | |
| EP | 3 095 380 A2 | 11/2016 | | |
| WO | WO 2006/136598 A2 | 12/2006 | | |
| WO | WO 2008/107324 A1 | 9/2008 | | |
| WO | WO-2009059351 A1 * | 5/2009 | ............ | A61B 5/053 |
| WO | WO 2010/122252 | 10/2010 | | |
| WO | WO 2013/075963 A1 | 5/2013 | | |

(Continued)

OTHER PUBLICATIONS

Search Report as issued in French Patent Application No. FR2114744, dated Sep. 6, 2022.

(Continued)

*Primary Examiner* — Eun Hwa Kim

(74) *Attorney, Agent, or Firm* — CUSHMAN PARTNERS

(57) ABSTRACT

A measurement station includes an electrocardiogram acquisition system, two control electrodes configured to contact a user, and an electrical connection circuit, the electrical connection circuit comprising a feedback loop connected to the two control electrodes.

22 Claims, 15 Drawing Sheets

(56) References Cited

FOREIGN PATENT DOCUMENTS

| WO | WO 2014/033105 A1 | 3/2014 |
|----|-------------------|--------|
| WO | WO 2015/036530 A1 | 3/2015 |
| WO | WO 2016/083432 A1 | 6/2016 |
| WO | WO 2020/081471 A1 | 4/2020 |
| WO | WO 2021/164561 A1 | 8/2021 |

OTHER PUBLICATIONS

Prutchi, D., et al., "Biopotential Amplifiers," Design and Development of Medical Electronic Instrumentation, Oct. 2004, XP055036136, pp. 1-40.
Pazhouhandeh, M. R., et al. "Two-electrode Impedance-sensing Cardiac Rhythm Monitor for Charge-Aware Shock Delivery in Cardiac Arrest," 2017 IEEE International Symposium on Circuits and Systems (ISCAS), May 2017, XP033156561, 4 pages.

* cited by examiner

106

702

R18

R16

R14

R12

R10

R8

R6

R4

R2

L17

L15

L13

L11

L9

L7

L5

L3

L1

Y

X

MEASUREMENT STATION WITH ELECTROCARDIOGRAM MEASUREMENT

CROSS-REFERENCE TO RELATED APPLICATIONS

This application claims priority to French Patent Application No. 2114744, filed Dec. 31, 2021, the entire content of which is incorporated herein by reference in its entirety.

FIELD

The present description relates to the monitoring of a user's health and more specifically to measurement stations for implementing one or more measurements of biometric signals (or physiological parameters) of a user.

BACKGROUND

Document WO2010/122252 discloses a connected scale with weight and bioimpedance measurement. Documents EP3087914 and EP3095380, on the other hand, disclose a connected scale for obtaining information on the user's cardiovascular status, including a PTT ("pulse transit time") measurement using a BCG and an IPG. Document WO2021/164561 discloses a scale with handle for measuring weight, performing a multi-channel ECG and performing a segmental BIA.

To obtain a quality ECG, one technique is to use a so-called "right leg drive" (RLD) electrode, which measures a potential of a user's body and then re-injects an amplified and inverted version of that potential.

WO2020/081471 describes a system with an electrode assembly for performing an ECG and an RLD electrode. Alternatively, this document proposes not to use an RLD and to use an AC-coupled signal input biased at mid-supply voltage.

In particular, obtaining a synchronized IPG and ECG is sought for various reasons: better identification of peaks, better knowledge of the user's vascular state, etc.

The paper "Estimation of Pulse Arrival Time Usinq Impedance Plethysmogram from Body Composition Scale" by Paliakatie et al. discloses a synchronized ECG and IPG. The ECG and IPG are acquired by two different systems but the synchronization is not described (wireless transmission is usually a source of difficulty).

The paper "Pulse arrival Time Estimation from the Impedance Plethysmogram Obtained with a Handheld device" by Gomez-Clapers et al. discloses a system with four electrodes in contact with the hands with a floating mass ("amplifier common") connected directly to the electrodes to obtain a synchronized ECG-1-channel (between the arms) and IPG. The system is localized and therefore less noisy, as explained in reference [15] ("Fast and Easy-to-Use ECG Acquisition and Heart Rate Monitoring System Usinq a Wireless Steering Wheel of this paper", Gomez-Clapers).

EP2737847 discloses a method comprising ECG and IPG measurement on the legs, using two independent circuits. The document does not go into further detail.

SUMMARY

Performing an ECG and IPG at the same time creates difficulties, especially when both measurements are performed by the same device. When the ECG is a multi-channel ECG with electrodes on the user's arm and legs (e.g., via a handle and scale), noise is usually more important.

An aspect of the present description aims to provide a measurement station that allows different measurements of biometric signals to be obtained with increased quality.

The invention is defined in the claims.

In an embodiment, the description presents a measurement station comprising:

- an electrocardiogram acquisition system, called ECG acquisition system,
- two control electrodes configured to contact a user's body,
- an electrical connection circuit, the electrical connection circuit comprising a feedback loop connected to the two control electrodes.

In an aspect of the invention, at least one of the following data is determined by the measurement station of the present application: weight or mass, electrocardiogram (ECG), impedance analysis (impedance analysis of the human body), including impedance- plethysmogram (IPG), impedance-cardiogram (ICG) and bioimpedance analysis (BIA), for the mass of fat, water, muscle, etc.), photoplethysmogram (PPG), ballistocardiogram (BCG), electrochemical skin conductance analysis ("ESC analysis" or simply "ESC" in the present description) and assessment of sweat function (sometimes referred to as "sudogram" in the present application), heart rate ("HR"), pulse wave velocity ("PWV"), etc.

In an embodiment, one of the two control electrodes is configured to measure a potential of the user's body, the feedback loop is configured to amplify and invert the measured potential, and the other of the two control electrodes is configured to set the user's body to the amplified and inverted potential.

In particular, the ECG acquisition system includes a plurality of ECG electrodes, configured to contact a user and an ECG electronic circuit, connected to the plurality of ECG electrodes. The plurality of ECG electrodes may include at least one electrode on the foot of the user and at least one electrode on the hands of the user or two electrodes on the two feet or two electrodes on the two hands. In one example, the ECG acquisition system includes three ECG electrodes, two on the hands and one on the left foot.

In an embodiment, the two control electrodes are separate from the plurality of ECG electrodes. In an embodiment, the electrical connection circuit is electrically independent of the ECG electronic circuit.

In an embodiment, the feedback loop comprises:

- an operational amplifier, and
- a feedback connection, connecting an output of the operational amplifier to an input of the operational amplifier, the feedback connection comprising at least one passive component.

In an embodiment, the passive component comprises a resistor and/or a capacitor.

In an embodiment, the control electrodes are connected to the input and output of the operational amplifier respectively.

In an embodiment, the measurement station comprises an impedance measurement system, the impedance measurement system comprising:

- a current source, for example alternating current,
- two current injection electrodes, for injecting a current into a user's body, the current source being connected to the electrical connection circuit and the two current injection electrodes being the two control electrodes.

In an embodiment, the measurement station comprises a switch for disconnecting the electrical connection circuit and the current source or in which the current source is able to be deactivated.

In an embodiment, the impedance measurement system comprises two measuring electrodes, adapted to measure a potential difference of a portion of the user's body through which a current generated by the current source flows.

In an embodiment, the ECG acquisition system and the impedance measurement system are configured to be activated simultaneously, to acquire a synchronized ECG and impedance measurement, for example an impedance-plethysmogram, IPG.

In an embodiment, the measurement station comprises a base adapted to receive a user's feet and on which is mounted at least one control electrode.

In an embodiment, the measurement station comprises a handle, which is suitable for receiving the hands of a user, and on which at least one of the ECG electrodes is mounted.

In an embodiment, the control electrodes are mounted on the base, two ECG electrodes are mounted on the handle, and one ECG electrode is mounted on the base.

The description also presents a method for acquiring an electrocardiogram, ECG, using a measurement station as described above, comprising the following steps:

E1: connecting the control electrodes to the electrical connection circuit, via a switch, E3: activating the ECG acquisition system to acquire an ECG.

In an embodiment, the following step is implemented before step E3 of activating the ECG acquisition system:

E2: deactivating the current source or disconnecting the current source from the electrical connection circuit.

The description also relates to a method for acquiring an electrocardiogram, ECG, and an impedance measurement, for example an IPG, using a measurement station as described above, comprising the following steps:

F1: connecting the control electrodes to the electrical connection circuit, via the switch, F3: simultaneously activating the ECG acquisition system and the impedance measurement system to acquire an ECG and an impedance measurement.

In an embodiment, the description also relates to a measurement station comprising:

an impedance measurement system comprising:
at least two injection electrodes for injecting a current into a user, and
an electrical connection circuit, the electrical connection circuit comprising a feedback loop connected to the two injection electrodes,
an electrocardiogram, ECG, acquisition system configured to acquire ECG signals,
a first control electrode, configured to change the potential of the user's body, wherein the first control electrode is one of the current injection electrodes.

In an embodiment, the measurement station comprises a second control electrode, the second control electrode being the other of the two current injection electrodes.

In an embodiment, the ECG acquisition system comprises:
a plurality of ECG electrodes, configured to contact a user,
an ECG electronic circuit, connected to the plurality of ECG electrodes, and wherein one of the control electrodes is one of the ECG electrodes.

In an embodiment, the description presents a measurement station comprising:

a base configured to receive a user's feet and comprising at least one foot electrode adapted to contact a user's foot,
a handle configured to receive a user's hands and comprising at least one hand electrode,
a detection system for detecting simultaneous contact of the user with the foot electrode and the hand electrode.

The detection system may generate data indicating that the detection has taken place and data indicating that the detection has not taken place, or it may simply not generate a signal.

In an embodiment, the sensing system is configured to set one of the two electrodes to a potential and to detect by the other electrode a potential above a threshold.

In an embodiment, the detection system comprises
a voltage generator capable of setting said electrode to the potential and
a voltmeter capable of measuring the potential of said electrode.

In an embodiment, the measurement station comprises a measurement acquisition system (BIA, ECG, IPG) using the two electrodes and the measurement station is configured to trigger the measurement acquisition system in case of detection of a simultaneous contact by the detection system.

In an embodiment, the measurement station comprises control circuitry configured to implement a predetermined sequence of measurements to be performed by one or more measurement acquisition systems (BIA, ECG, IPG), wherein measurements requiring the handle are not performed in the absence of simultaneous contact detection by the detection system.

The control circuitry may be switched from one measurement to another, without the need to measure with the handle.

In an embodiment, the measurement station comprises control circuitry configured to implement a predetermined sequence of measurements to be performed by one or more measurement acquisition systems (BIA, ECG, IPG), the measurements requiring the handle being performed upon detection of a simultaneous contact by the detection system.

In an embodiment, the measurement acquisition system comprises an ECG acquisition system or an impedance measurement system.

In an embodiment, in response to the sensing system not detecting a simultaneous contact, the ECG acquisition system is not activated.

In an embodiment, the measurement station comprises control circuitry capable of implementing the following steps:
imposing a potential on an electrode (in the foot for example)
measuring the potential at the other electrode,
determining that the measured potential is at least equal to a predetermined threshold, the threshold being dependent on the imposed potential (the threshold being, for example, equal to the value of the imposed potential minus a user's body loss value).

In an embodiment, in response to detecting a simultaneous contact by the sensing system, the control circuitry enables a measurement acquisition using the handle electrodes.

In an embodiment, the potential is between 0.5V and 2V.

In an embodiment, the base comprises a weight measurement system including a weight sensor and the measurement station is configured to activate the detection system in response to a weight detection by the weight measurement system.

In an embodiment, the measurement station comprises control circuitry storing a measurement sequence comprising handle measurements and non-handle measurements and a measurement sequence comprising only non-handle measurements, wherein the control circuitry is configured to switch from one sequence to the other depending on detecting by the detection system. In particular, if the detection system detects the simultaneous contact, then the control circuitry selects the full sequence of measurements.

The present description also relates to a method for detecting a contact between the user and the electrodes, using the previously described measurement station.

DESCRIPTION OF THE FIGURES

The following figures illustrate the elements described in this description.

DETAILED DESCRIPTION

Figure 1:
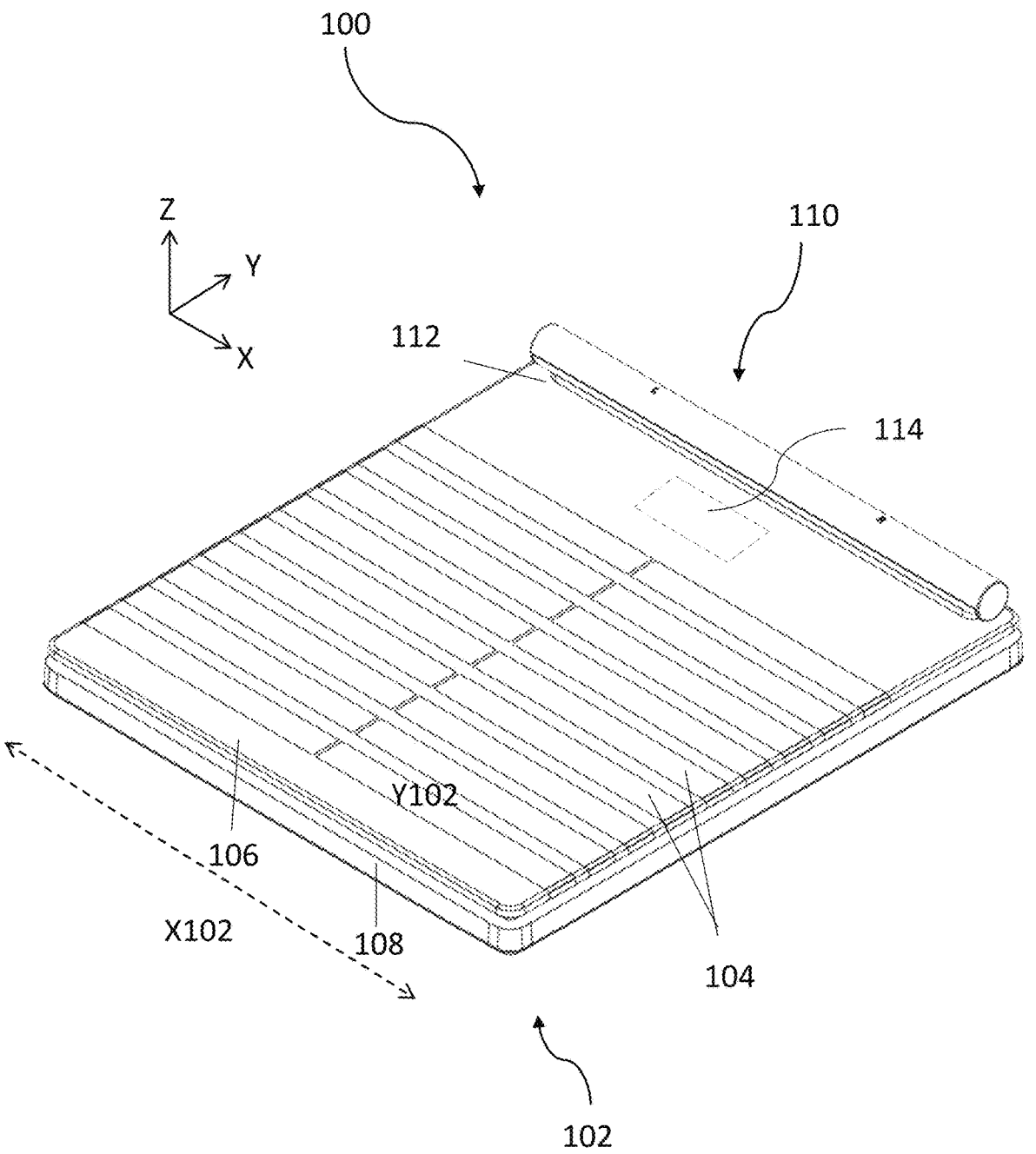
FIG. 1 shows a three-dimensional view of a measurement station with a handle, according to an embodiment.

FIGS. 1 to 4 illustrate an embodiment of a measurement station 100 according to at least one embodiment of the present description. The measurement station 100 is substantially in the form of a base 102 on which a user may place his or her feet, for example flat. The user may be on the measurement station or sitting on a chair. In the normal position of use, the user's feet are placed flat on the measurement station 100. The thickness of the base 102 is, for example, less than 10 cm or even 6 cm. The measurement station 100 includes one or more sensors 104 suitable for measuring physiological information of a user.

In an embodiment, some sensors 104 (e.g., electrodes) are mounted on a substrate 106 of the base 102, the substrate being configured to receive a user's feet. The substrate may be a rigid plate, as shown in the Figures, and referred to as a measurement plate 106. The measurement plate 106 defines a plane parallel to an XY plane. The measurement plate 106 may be made of glass. Nevertheless, the substrate may be deformable under the weight of the user. The substrate 106 may be mounted on a base frame 108, such as a rigid base, or legs (not shown). In the case of a base 102 functioning as a bathroom scale, sensors are positioned between the substrate 106 and the base frame 108 (so-called "sandwich" architecture) or between the substrate 106 and the feet (so-called "foot" architecture). The sensors may be load cells (typically four) that provide a weight, and thus a mass of a user. The base frame 108 may be made of metal or plastic.

Figure 2:
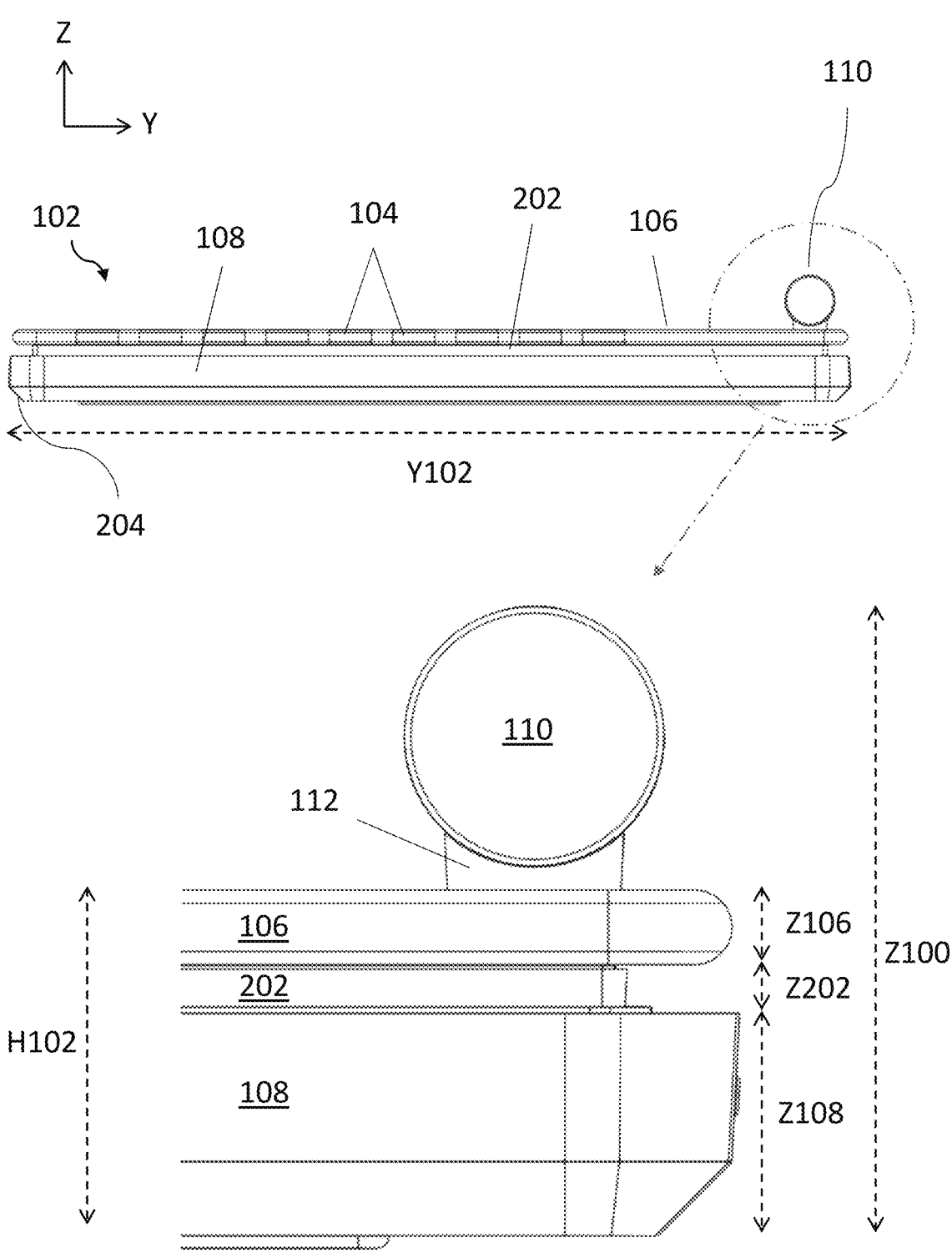
FIG. 2 shows a side view of the station of FIG. 1.

As visible in FIG. 2, the measurement station 100 includes a support plate 202, which may be integral with the measurement plate 106. The support plate 202 is designed to accommodate a portion of the electronics of the measurement station 100. The support plate 202 is positioned between the base frame 108 and the measurement plate 106.

In a legged architecture, two structural groups are defined that move in relation to each other: the legs on the one hand (fixed group), and everything else on the other hand (mobile group). The load cells mechanically connect these two groups. The support plate, if present, is then generally hidden by an external cover integral with the measurement plate. Visually, only the moving part is usually visible.

In a sandwich architecture, two groups are defined that move in relation to each other: the base frame 108 and the elements associated with it on the one hand (fixed group), and everything else on the other (mobile group). The load cells mechanically connect these two groups. Visually, the two groups are generally visible.

Figure 3:
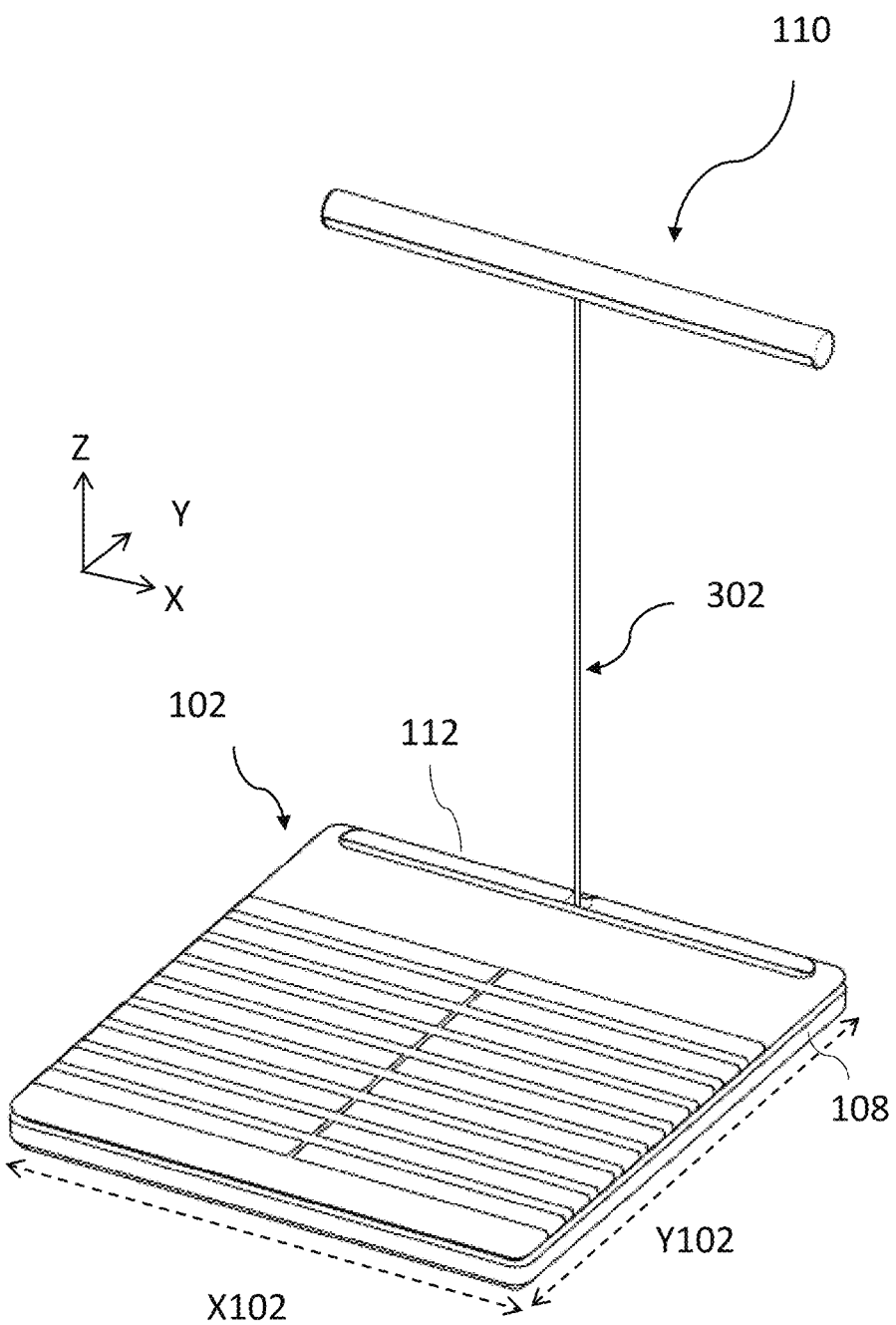
FIG. 3 shows a three-dimensional view of the station of FIG. 1, but with the handle in the extended position.
Figure 4:
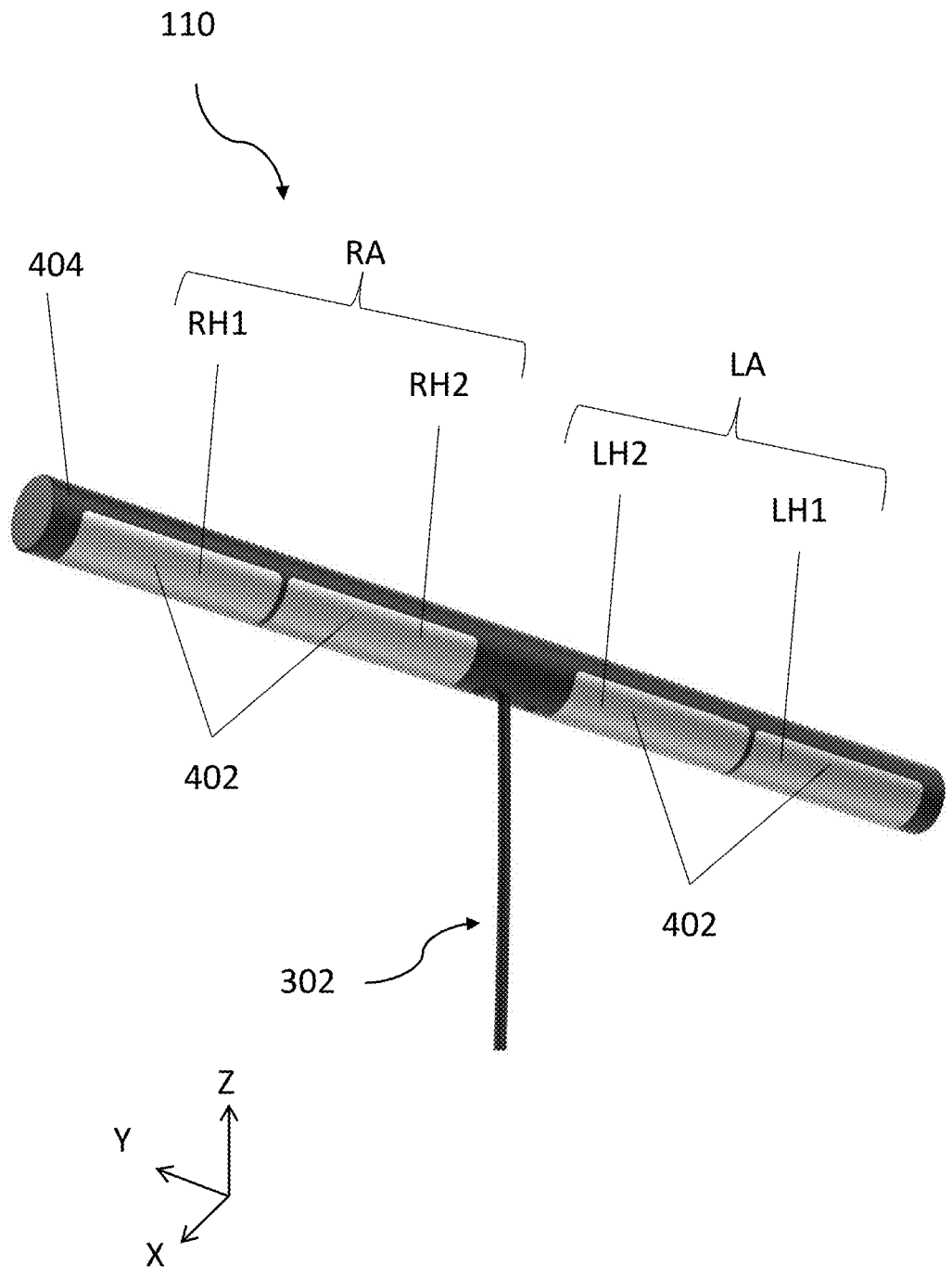
FIG. 4 shows a detailed view of the handle.

In an embodiment, the measurement station 100 further comprises a handle 110, suitable for gripping by at least one hand of the user, shown in FIGS. 3 and 4. The handle 110 may be connected to the measurement station by a cable 302 (visible in FIG. 3). In order to have a convenient measurement station 100 without a flying cable, the cable 302 may extend and retract (e.g., wind up and down) within the base 102. For this purpose, a reel (not visible the Figures) is arranged in a space provided between the substrate 106 and the base frame 108. At least two positions are thus defined for the handle: a stowed position (visible in FIGS. 1 and 2) and an extended position (visible in FIG. 3). Thus, the handle is movable at least between the stowed position and the extended position. The base 102 further includes a handle support 112 that may accommodate the handle 110 in the stowed position. The handle support 112 is, for example, mounted on the substrate 106. It will be described in more detail later. The handle 110 also includes at least one sensor 104, which is referenced 402.

The handle 110 is used to perform at least one of the following measurements: ECG (ECG-1-channel between the two hands or multiple channels with other limbs), BIA (so-called "segmental"), IPG. The sensors 402 of the handle 110 are selected in particular from: optical sensor for PPG and electrodes.

The base 102 may include a display 114 (e.g., a screen or an LED or e-ink display) to display information to the user. The display 114 is shown dotted in FIG. 1 because, in the example of the Figures, it is located below the measurement plate 106 and is not or only minimally visible when turned off.

The base frame 108 of the base 102 may include a chamfer 204 to facilitate gripping the measurement station 100 while on the ground.

In an embodiment, the base 102 has a substantially rectangular shape in an XY plane. For example, the base 102 has a substantially parallelepiped shape in XYZ space.

When the measurement station 100 is positioned flat, the measurement plate 106 is parallel to a plane XY. The measurement station 100 includes a longitudinal direction in a plane XY and a transverse dimension in a plane XY and orthogonal to the longitudinal direction. By height is meant the dimension along the Z axis (also called thickness); by width is meant the transverse dimension along the X axis; by length is meant the longitudinal dimension along the Y axis. In normal use, the user's feet are positioned along the length Y of the base 102. The edge of the measurement station 110 (or base 102, or measurement plate 106) that is closest to the front part of the foot in normal use (i.e., the toes) is referred to as the front edge, and the opposite edge of the measurement station 110 (or base 102, or measurement plate 106) that is closest to the rear part of the foot in normal use (i.e., the heel) is referred to as the rear edge. A median axis may be defined, along the length Y (longitudinal, therefore), about which the measurement plate 106 is symmetrical and which makes it possible to define a left portion, intended for the left foot, and a right portion, intended for the right foot. The width X102 of the base 102 may be between 330 mm and 400 mm, limits included (for example, about 357 mm) and the length of the base Y102 may be between 300 mm and 360 mm, limits included (for example, about 325 mm). The term "about" as used herein covers value deviations of +/−5%. The length and/or width of the measurement plate 106 may be slightly less than the length and/or width of the base frame 108, such that the measurement plate 106 is slightly recessed from the base frame 108. In this case, the length and width of the base frame 108 correspond to the length and width given above for the base 102, respectively. Such a design protects the measurement plate 106 from impact and contact with the external environment. The application FR2106653, incorporated by reference, describes such a solution. The term "slightly" as used herein covers a value difference of less than 10%, for example less than 5%.

Specifically, as illustrated in FIG. 2: the height H102 of the base 102 may be between 20 mm and 35 mm, limits included (e.g., between 35 mm and 40 mm, limits included), and the maximum height Z100 of the measurement station 100 may be between 45 mm and 55 mm, limits included (e.g., 51 mm). As illustrated in the Figures, only the handle support 112 and the handle 110 protrude along the Z direction from the measurement plate 106. Detailing the various dimensions: the height Z108 of the base frame 108 may be between 10 mm and 20 mm, limits included (e.g. 18 mm), the height Z202 of the support plate 202 may be between 3 mm and 6 mm, limits included (e.g. 4 mm), the height Z106 of the measurement plate 106 may be between 4 mm and 8 mm, limits included (e.g. 6 mm).

The cable 302 may be between 50 cm and 120 cm long, limits included. The length is chosen so that most users may grip the handle while standing with their hands down (at rest).

The measurement station 100 may, however, have different shapes and/or dimensions, provided that the shape and/or dimensions allow for the measurements herein described to be obtained. In particular, the base 102 may have an oval or more rounded shape in the XY plane.

The measurement station 100 may have a mass of between 3 kg and 6 kg, limits included (for example between 4 kg and 5 kg, limits included).

Using the sensor(s) on the base 102 and/or the sensor(s) on the handle 110, the measurement station 100 may perform a group of measurements on the user. In particular, the sensors 104 used include electrodes that are formed from electrically conductive paths mounted on the substrate 106 and/or the handle 110 (metal inserts, metal deposits, etc.). Some measurements may require only sensors on the base 102, other measurements may require only sensors on the handle 110, other measurements may require sensors on the handle 110 and the base 102 simultaneously.

The measurement station 100 may perform an ECG using the handle 110 (e.g., a single channel ECG), or an ECG using the handle 110 and the base 102 (e.g., a multi-channel ECG, such as a six-channel ECG). The measurement station 100 may also perform a BIA body impedance analysis using the handle 110 and/or the base (inter-leg BIA and/or segmental BIA). The measurement station may perform an IPG in the leg arch ("between legs") or IPG in the foot ("in the foot").

The sensors may comprise electrodes adapted to: measure and/or apply a voltage (DC or AC) and/or a potential (DC or AC), and/or inject and/or recovere a current (DC or AC). The functions of these electrodes may be selected from the following list: i+ and i−, for injecting AC current into a user's body; V+ and V−, for measuring a potential difference in a user's body; RA, LA and LL, for measuring an electric current. The i+ and i−, V+ and V− electrodes are used for a BIA, IPG or ICG; the RA, LL, LL electrodes are used for an ECG.

In particular, the measurement station 100 is configured to perform different measurements. Since the number of electrodes is limited (due to area and number considerations), the measurement station 100 may have a particular arrangement of electrodes.

As noted above, the sensors may include load cells, whereby the measurement station 100 may measure a weight and perform a BCG.

The handle 110 is illustrated in detail in FIG. 4. The handle 110 allows the measurement station 100 to perform a wider variety of measurements or alternatively more comprehensive measurements through electrical connection with at least one or even both hands. In particular, segmental BIA and/or multi-channel ECG are made possible by the addition of the handle 110 to the base 102. The sensors 402 of the handle 110 include, for example, electrodes adapted to measure and/or apply a voltage and/or a potential and/or inject and/or recovere a current.

In an embodiment, the handle 110 includes four electrodes, arranged in two pairs: a pair for the left hand and a pair for the right hand. For this purpose, the electrodes of the handle are referred to as: electrodes LH1, LH2, side by side on a left part of the handle 110 and electrodes RH1, RH2, side by side on a right part of the handle (by left part, respectively right part, is meant the part of the handle intended to be in contact with the left hand, respectively right hand). "Side by side" here means with a space between the electrodes, to insulate the electrodes from each other. Thus, the electrodes are arranged in succession between two ends of the handle 110. When the handle 110 is straight, the electrodes are arranged in sequence along the main direction of the handle 110. The electrodes LH1 and RH1 are positioned axially on the side of one end of the handle; the electrodes LH2, RH2 are positioned axially on the side of the center of the handle. Thus, in order, there are the following electrodes: LH1, LH2, RH2, RH1.

In an embodiment, the sensors 402 of the handle 110, when they are electrodes, are made as a plurality of metal inserts in the handle 110. Materials that may be used for the metal inserts include stainless steel, titanium, brass, ITO (indium tin oxide), nickel (or nickel alloy), or conductive plastics. For signal processing and/or acquisition, in particular ECG, the handle 110 may include processing electronics (amplification, filtering, etc.), particularly for ECG. It is generally desirable to amplify the signal as close to the electrodes as possible because the cable may pick up ambient noise.

To perform a modular segmental BIA (to obtain data on both arms), four 402 electrodes are required. To perform an ECG, two 402 electrodes are required.

Figure 5:
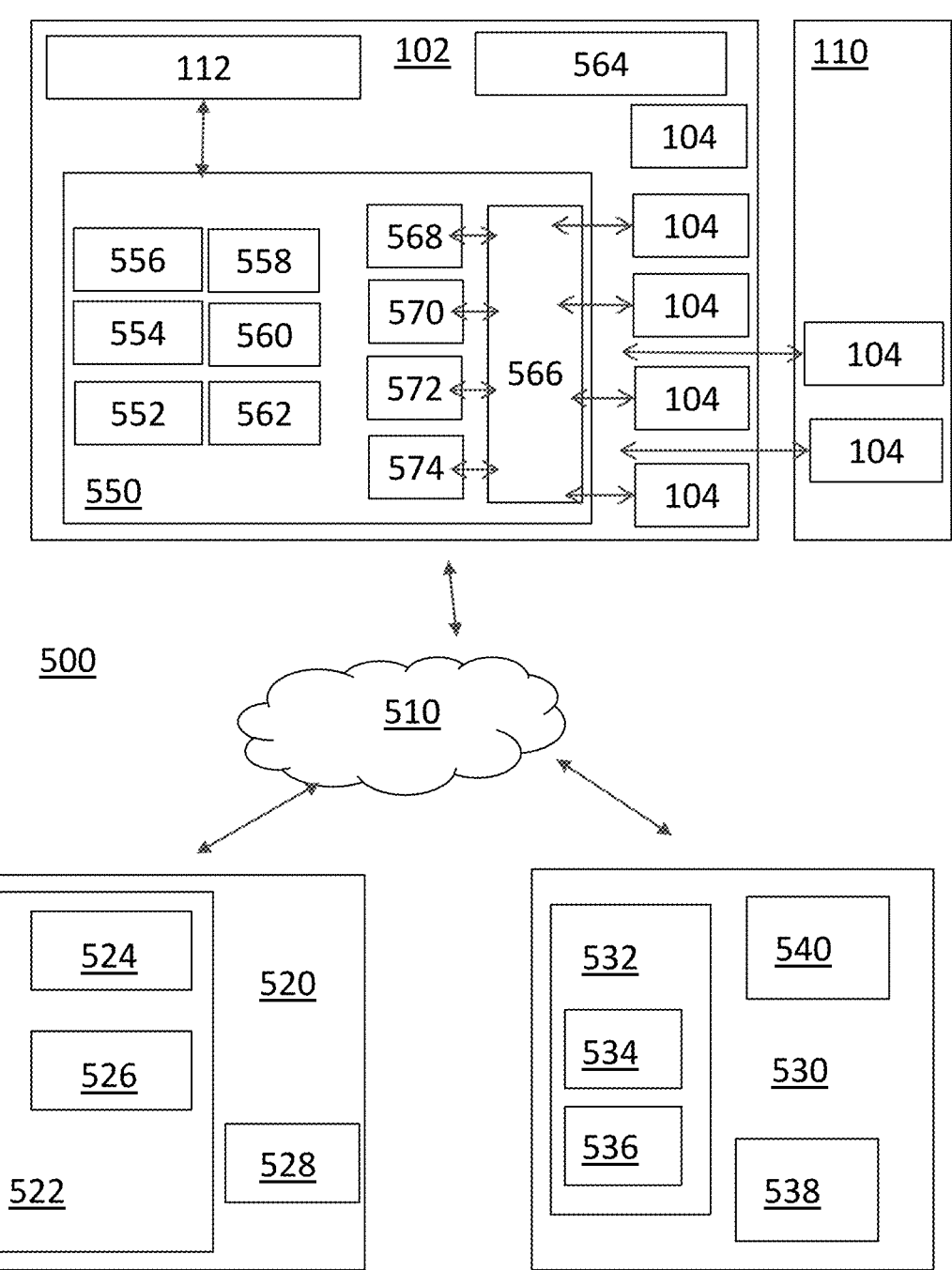
FIG. 5 shows a schematic view of the measurement station and its surroundings.

FIG. 5 illustrates a schematic view of the overall architecture 500 into which the measurement station 100 may be inserted. This overall architecture forms a system comprising the measurement station 100. In particular, the measurement station 100 may communicate with third party devices via a communication network 510, which is for example a wireless network (in particular a network compatible with at least one of the following communication protocols: Bluetooth, Wi-Fi, cellular, etc.). The third-party devices may include a server 520 and a mobile terminal 530 (smartphone, etc.). The server 520 may include control circuitry 522, including a processor 524 and a memory 526, and an input/output ("I/O") interface 228, which enables the control circuitry to receive and send data to the communication network 510. The memory 526 may store code instructions, which, when they are executed by the processor 524, perform various functions of the server 520. The mobile terminal 530 may include control circuitry 532, including a processor 534 and a memory 536, and include an input/output (I/O) interface 538, which enables the control circuitry to receive and send data. The memory 536 may store code instructions, which, when they are executed by the processor 534, perform various functions of the mobile terminal 530. The server 520 is a remote server, for example, located in a data center. The mobile terminal 530 further includes a user interface 540 ("UI") configured to display information to the user and allow the user to enter information (such as height, gender, etc.), if necessary. In particular, the control circuitry 532 is configured to run an application managing the environment of the measurement station 100. The mobile terminal 530 is a personal object of the user, typically in close proximity to the user.

The measurement station 100 may communicate with the server 520 and/or the mobile terminal 530. In an embodiment, the measurement station 100 may communicate directly with the mobile terminal 530, for example via Bluetooth or Bluetooth Low Emission (BLE). This communication may be implemented at the installation of the measurement device 100, in particular to pair it with the mobile terminal 530 and/or to configure a connection to the server 520 that does not transit through the mobile terminal 530 and/or as a backup for a failed communication with the server 520. In an embodiment, the measurement station 100 may communicate directly with the server 520, without transiting through the mobile terminal 530. This communication allows the user to use the measurement station even without having his mobile terminal 530 nearby.

The measurement station 100 also includes control circuitry 550 with a processor 552 and a memory 554, and an input/output (I/O) interface 556, which allows the control circuitry to, among other things, receive and send data to the communication network 510. The processor 552 is configured to, among other things, process data obtained by the sensors 104. In particular, the processor 552 may execute instructions from a program stored in the memory 554. The control circuitry 550 may include a microcontroller, which integrates the processor 552, the memory 554 and the input/output interface 556. The control circuitry 550 may further include an analog front end ("AFE") device. The control circuitry 550 may also include an analog to digital converter ("ADC"). The measurement station 100 includes a voltage source (e.g., DC) 558 and a current source 560 (e.g., AC). The measurement station 100 also includes a voltmeter 562 (or any system for measuring a voltage). The voltmeter 562 may be integrated with the AFE. The current source 560 may be integrated with the AFE and the voltage source 558 may be integrated with the microcontroller MCU (e.g., via a digital-to-analog converter DAC). Some of the sensors 104 (in particular the sensors 402 of the handle in FIG. 4 or the electrodes 602 of the base 102 in FIG. 6) are connected to the control circuitry 550 (e.g., to the MCU or to the AFE). The measurement station 100 includes a battery 564, suitable for supplying power to the various components of the measurement station 100.

The control circuitry 550 and other electronic components may be mounted on a printed circuit board ("PCB"), for example attached to the support plate 202. Connectors connect the electrical conductive paths from the measurement plate to the PCB. In order to change the connections of the electrodes to the various components of the measurement station 100, the measurement station includes a switch 566. The switch 566, which may include a plurality of switches controlled by the microcontroller MCU, will be described in more detail later).

The monitoring circuitry 550 includes, for example, an ECG acquisition system, an impedance measurement system (for BIA or IPG), and in particular an ESC system (for assessing skin sweat function, by performing an electrochemical skin conductance ESC). In addition, the control circuitry 550 may include a user presence detection system to assess whether a user's body is in contact with the electrodes. The ECG acquisition system includes electrodes (shown as 602 in FIGS. 6 and 402 in FIG. 4) and an ECG electrical circuit 568 (including various amplification and/or filtering stages and a demodulator); the impedance measurement system includes, in particular, electrodes (represented by 602 in FIGS. 6 and 402 in FIG. 4), the current source 560, the voltmeter 562 and an impedance measurement electrical circuit 570 that connects the electrodes to the current source and to the voltmeter (which incorporates various amplification and/or filtering stages); the ESC system includes electrodes, the voltage source 558, and an ESC electrical circuit 572 (which incorporates various electronic components, including resistors); the sensing system includes electrodes, the voltage source 558, the voltmeter 562, and a sensing electrical circuit 574 (which connects the electrodes to the current source and the voltmeter (which incorporates various amplification and/or filtering stages). The switch 566 allows the sensors 104, e.g. electrodes to be connected to, inter alia, the various aforementioned circuits 568, 570, 572, 574, or to disconnect all sensors and/or the electrodes from the control circuitry 550.

The control circuitry 550 is essentially located in the base 102, except for a few components (amplification, filtering and switches) located in a PCB in the handle 110, to process the signals before they are passed through the cable 302.

As previously mentioned, the measurement station 100 also includes the display 114, such as a screen (OLED/PMOLD, Retina, etc.), for displaying information to the user. Alternatively, the measurement station 100 does not include a display.

Figure 6:
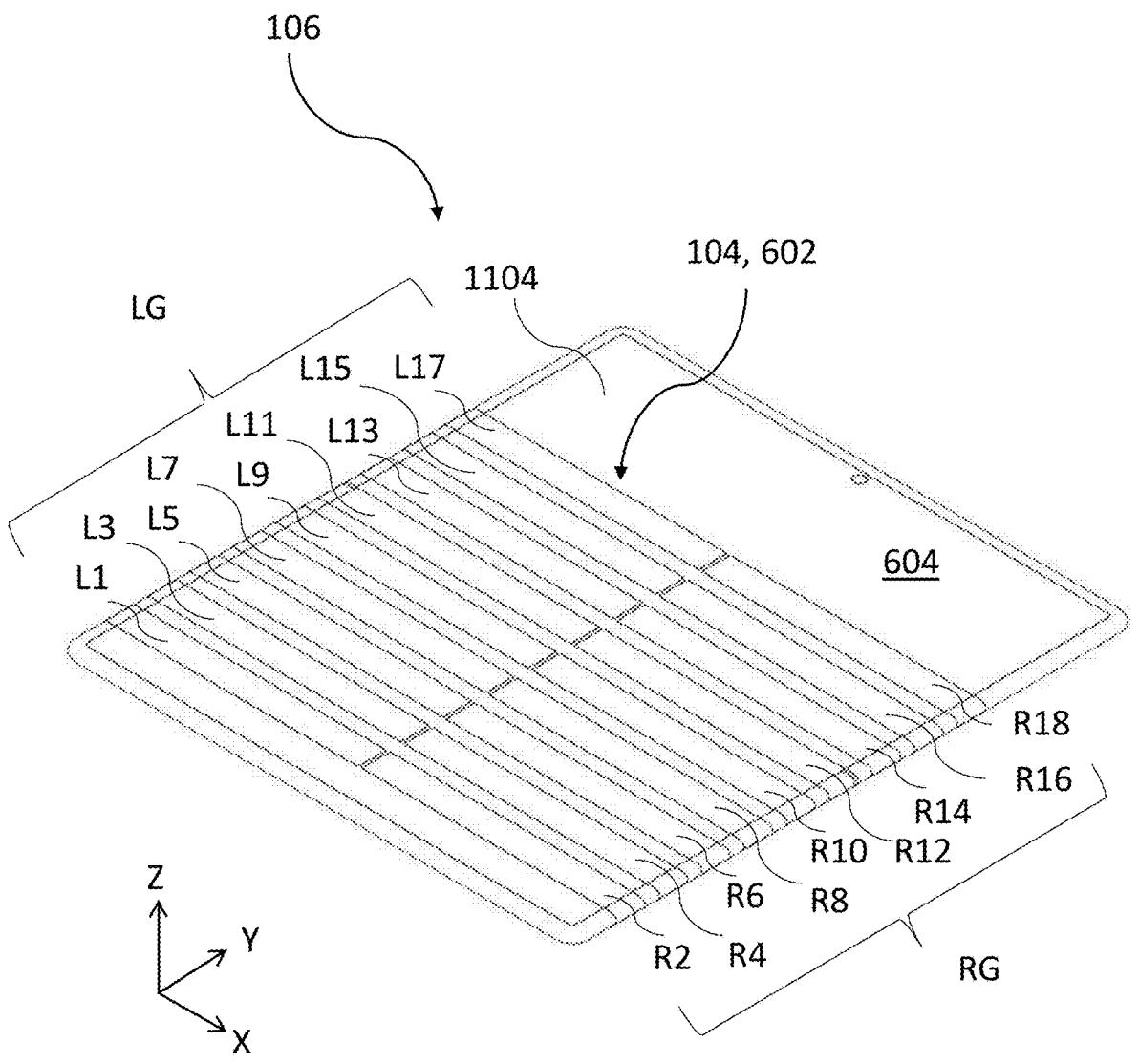
FIG. 6 illustrates a three-dimensional view of an isolated measurement plate.
Figure 7:
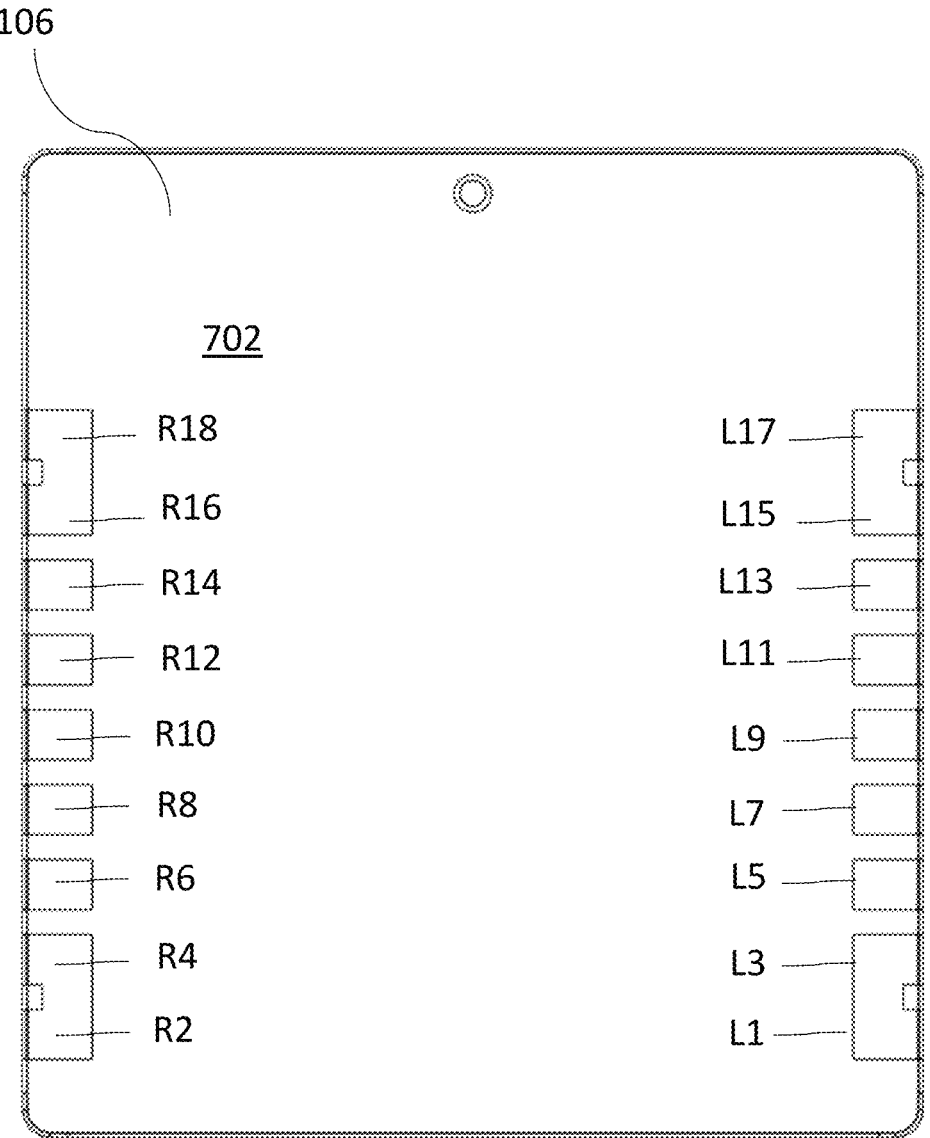
FIG. 7 illustrates a view from below the measurement plate of FIG. 6.
Figure 7:
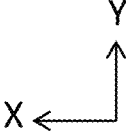

In an embodiment, the sensors 104 include electrically conductive paths 602 (referred to as "electrodes") on the base 102 (see in particular FIGS. 6 and 7). The electrodes 602 may take the form of a metallic deposit on at least one top face 604 of the measurement plate 106. The upper face

604 of the measurement plate 106 is defined as the face receiving the user's feet (the outer face that is visible). To provide electrical connection to the PCB, the electrodes 602 may pass through an edge of the measurement plate 106 and extend to a lower face 702 of the measurement plate 106. The relevant edge(s) of the measurement plate 106 may have a rounded shape to ensure that the metal deposition is properly completed, and electrical continuity is ensured. In addition, a rounded edge helps to avoid the risk of injury when gripping the measurement station 100. By rounded edge is meant a circular arc or similar shapes. The rounded edge also simplifies the metal deposition during manufacturing. Application FR2106653, incorporated by reference, describes these electrically conductive paths in detail.

The electrodes 602 are connected to the PCB via an electrical connector, which provides a connection between the electrically conductive path on the bottom surface 702 and the PCB mounted on the support plate 202. The switch 566 allows the electrodes to be connected and disconnected to the various systems (ECG acquisition system, impedance measurement system, sudogram system, etc.). In this way, each electrode may have several different functions depending on the switching position of the switch 566. For example, the switch 566 comprises a plurality of switches controlled by the microcontroller MCU.

The top surface 604 of the base 102 includes a left group LG of electrodes (intended to be in contact with the left foot, and a right group RG of electrodes intended to be in contact with the right foot. When the base 102 is set down in normal use, the user places his feet on a left side of the scale and a right side of the scale (with the toes on the display side 114). FIGS. 6 and 7 show electrically conductive paths L1, L3, L5, L7, L9, L11, L13, L15, L17 which form the electrodes of the left group LG of electrodes and electrically conductive paths R2, R4, R6, R8, R10, R12, R14, R16, R18, which form the electrodes of the right group RG of electrodes.

The electrodes 602 may take the form of strips parallel to each other along the X direction (the strips extend along the X width of the base 102).

In the illustrated architecture, the pairs of electrically conductive paths L1 and L3; L15 and L17; R2 and R4; R16 and R18 are not independent but are permanently electrically connected, so that the base 102 includes in practice seven independent electrodes in the left group LG and seven independent electrodes in the right group RG. These permanent electrical connections may be made via the electrical paths on the measurement plate 106 (e.g., on the bottom side 702, not shown) or via the PCB of the measurement station 100.

In an example, the electrically conductive paths on the top side 604 corresponding to the electrodes have a dimension (on the top side 604) along the length Y of between 1.5 cm and 2 cm, limits included (e.g., 1.7 cm); the spacing between two strips may be between 0.5 cm and 1 cm, limits included (e.g., 0.85 cm); and the electrodes may have a dimension along the width X of greater than 10 cm.

In particular, each group LG, RG may comprise at least four independent electrodes to be able to perform, in particular, an IPG in the foot (two electrodes connected to the AC source 560 and two electrodes connected to the voltmeter 562). In another embodiment, each LR, RG group may include at least two independent electrodes (to perform an ESC with anode/cathode and a high impedance electrode, or to perform a BIA or IPG between the legs), or three independent electrodes.

In an embodiment, the measurement station 100 may perform an electrocardiogram, ECG. For this purpose, the sensors 104 of the measurement station 100 (base 102 and handle 110) may include a plurality of conductive surfaces for detecting electrical currents flowing through a user's body. The measurement station 100 includes an ECG electrocardiogram acquisition system, implementing some of the sensors 104.

On the base 102 illustrated in particular in FIG. 6, these conductive surfaces take the form of parallel strips L1 to L17 and R2 to R18. In particular, the base 102 includes two groups of electrodes: a first group of electrodes LG, which is positioned on a left portion of the base 102 in normal use (referred to as the left group, but this term should not be interpreted restrictively for a left foot only), and a second group of electrodes RD, which is positioned on a right portion of the base 102 in normal use (referred to as the right group, but this term should not be interpreted restrictively for a right foot only). In particular, a user may ride upside down on the base 102 (left foot on the right group RG and right foot on the left group LG). FIGS. 1 and 6 illustrate an example of an embodiment of the right and left groups LG, RG.

On the handle, these conductive surfaces take the form of four electrodes RH1, RH2, LH2, LH1. In the ECG configuration, the electrodes RH1, RH2 and LH1, LH2 may be connected in pairs, so that the handle comprises two electrodes RA ("right arm"), LA ("left arm"). Alternatively, only one of RH1, RH2 and LH1, LH2 may be connected to the ECG acquisition system.

With these sensors 104, the ECG measurement station may perform a multi-channel ECG using three measurement electrodes: a left hand electrode (LH electrode), a right hand electrode (RH electrode) and an electrode in the foot, for example in the left foot (LL electrode). The LL electrode may be formed by at least one strip of the LG group (e.g., strips L15, L17 of the base 102).

In an embodiment, the ECG acquisition system 1010 may measure the DII (between the RA and LL electrodes) and DIII (between the LA and LL electrodes) channels and may calculate the other channels (DI, aVF, aVL, and aVR).

Alternatively, the measurement station 100 may perform a single-channel ECG using two measurement electrodes: for example, between the arms with a left hand electrode (LH electrode) and a right hand electrode (RH electrode); for example, between the legs with a left foot electrode (LL electrode) and a right foot electrode (RL electrode). The RL electrode may be formed by at least one strip of the RG group (e.g., the R16, R18 strips of the base 102).

During an ECG, the user's body may be grounded to a virtual earth potential to prevent the operational amplifiers of the ECG acquisition system from saturating. For example, the LL electrode may be used to set this potential.

Figure 8:
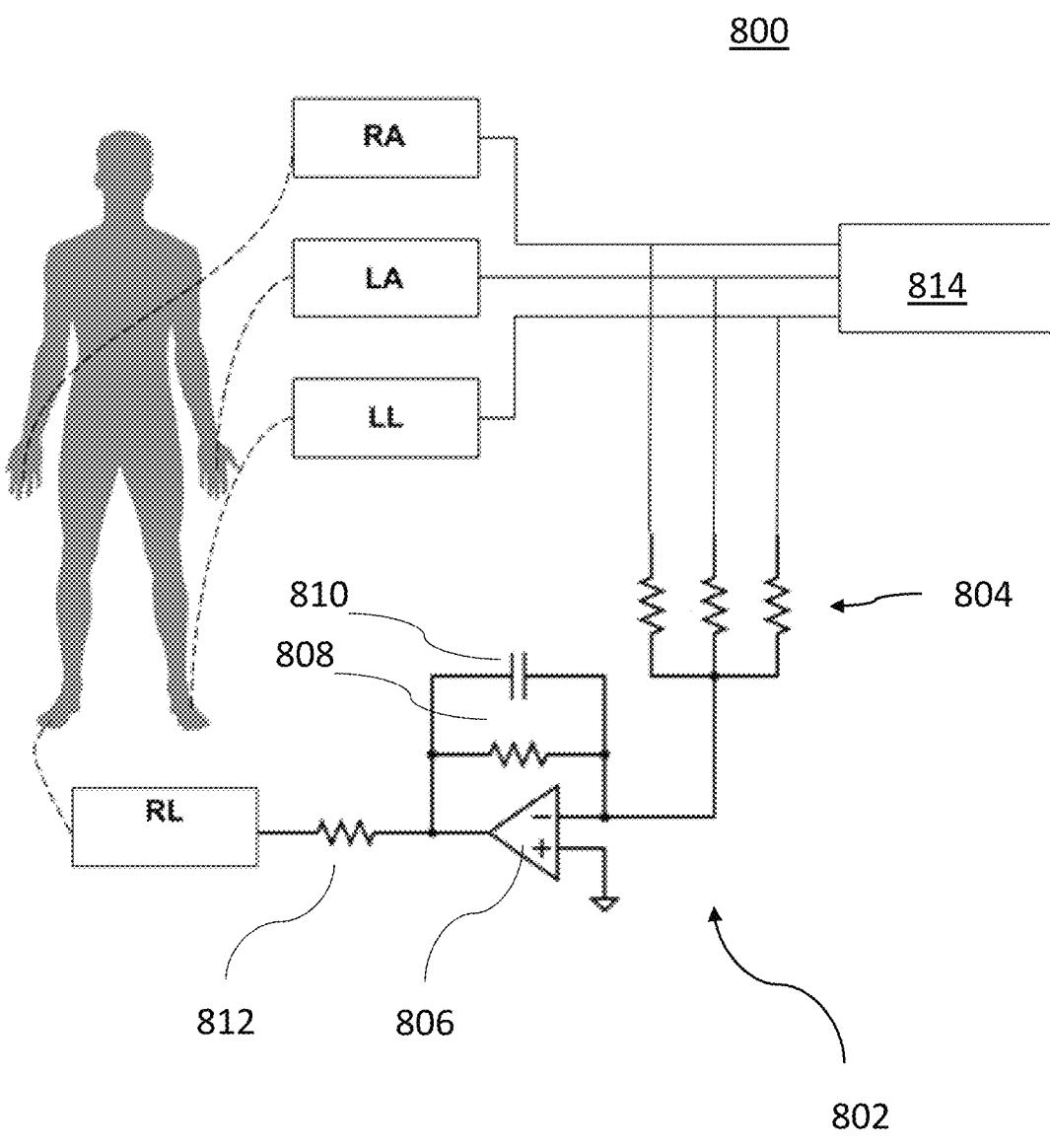
FIG. 8 illustrates a view of an ECG acquisition system with an RLD electrode.

In an embodiment, the measurement station 100 comprises, in an ECG arrangement 800, an RLD circuit 802 ("right-leg drive"), illustrated in FIG. 8. The RLD circuit 802 is illustrated in the case of a multi-channel ECG with the electrodes LA, RA and LL. The principle consists in measuring the so-called "common-mode voltage Vcm", then reinjecting an amplified and inverted form of this measured voltage into the body. This voltage Vcm is also called "Wilson Common Terminal, WCT". The three potentials of electrodes RA, LA, LL are averaged using resistor(s) 804 and then sent to the negative input of an operational amplifier 806. The virtual ground is sent to the positive input of the operational amplifier 806 to form a potential reference to which it is desired to set the user. A feedback line with a feedback resistor 808 (about 1 MOhm) and a feedback capacitor 810 (to set the open loop gain, about 1.5 nF) is provided between the negative input and the output of the operational amplifier 806. Finally, the electrode RL is connected to the output of the operational amplifier 806 through a resistor 812 to limit the current that may flow through the user's body. The electrodes RA, LA, LL are connected to an ECG electronic circuit 814.

The RLD 802 circuit described above provides a better quality ECG signal than devices without the RLD circuit. Nevertheless, to obtain synchronized measurements, it may be desirable to perform an ECG at the same time as another measurement. This other measurement may involve injecting a current into the user's body: for example, in the case of an IPG.

In the case of an IPG, a current source injects a current into the user's body and a voltmeter measures a voltage drop across the body induced by this current. An impedance measurement system thus includes the current source and a feedback loop to maintain the voltage Vcm within the operating range of the amplifiers.

Figure 9:
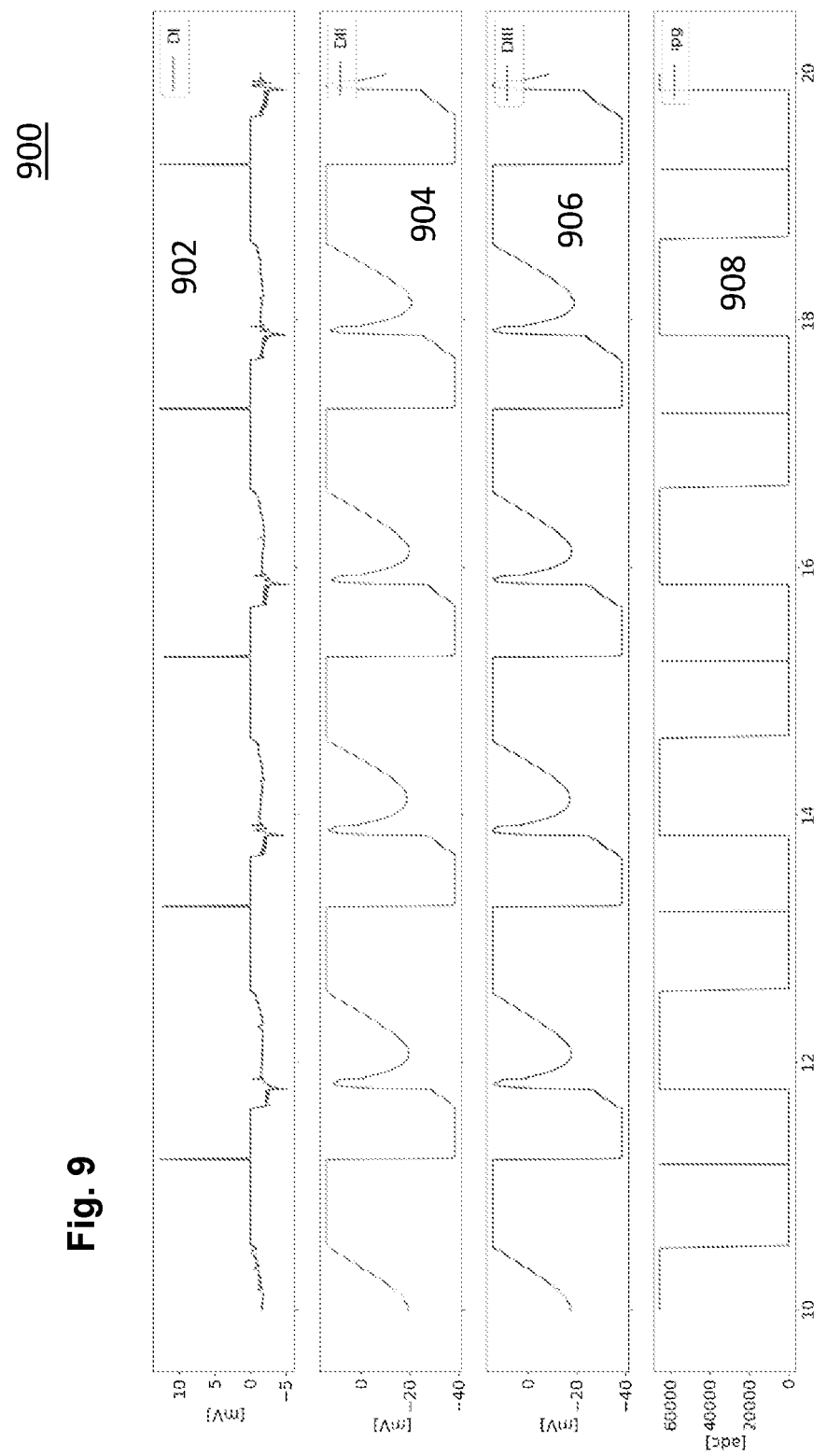
FIG. 9 shows ECG measurements with an RLD electrode.

When IPG and ECG are performed at the same time, there are two feedback loops (that of the RLD 802 circuit and that of the impedance measurement system) that are activated and generate disturbances that affect the measurements made (even saturating the operational amplifiers). FIG. 9 shows results 900 of an ECG with RLD measured at the same time as a current injection for IPG. The DI lead (between RA and LA) 902, the DII lead (between RA and LL) 904, the DIII lead (between LA and LL) 906 and the voltage obtained for IPG 908 are shown. The signals are not usable: for the IPG, no peak blood flow is visible (saturation), and the ECG signals are also saturated.

Figure 10:
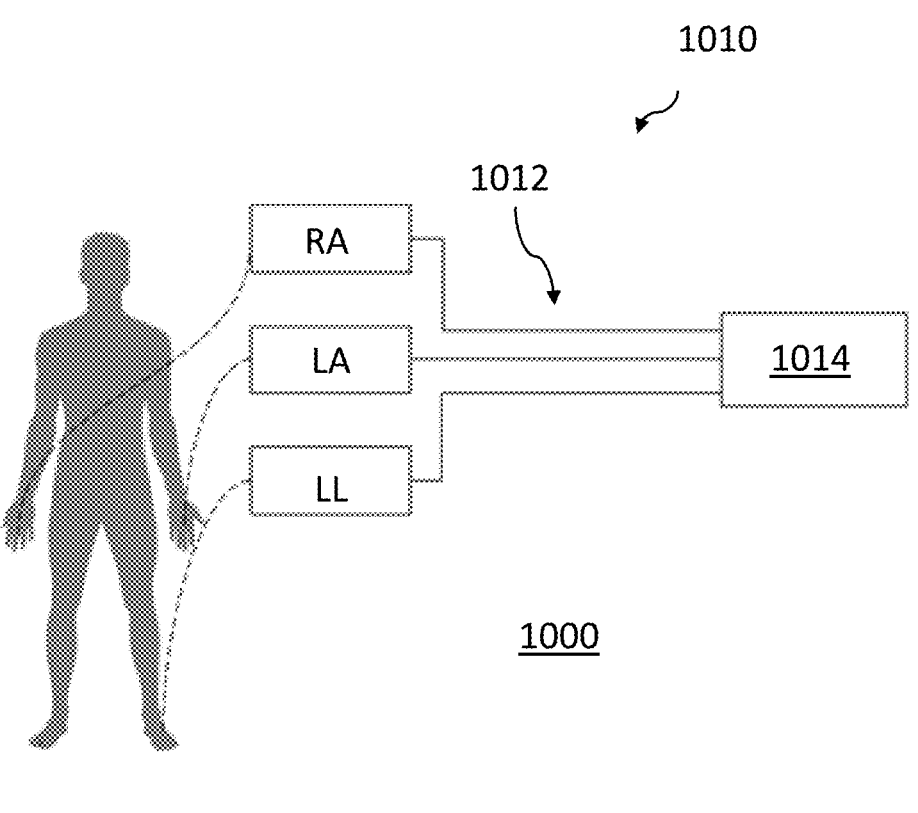
FIG. 10 illustrates a schematic view of an ECG acquisition system with a feedback device according to an embodiment of the invention.
Figure 10:
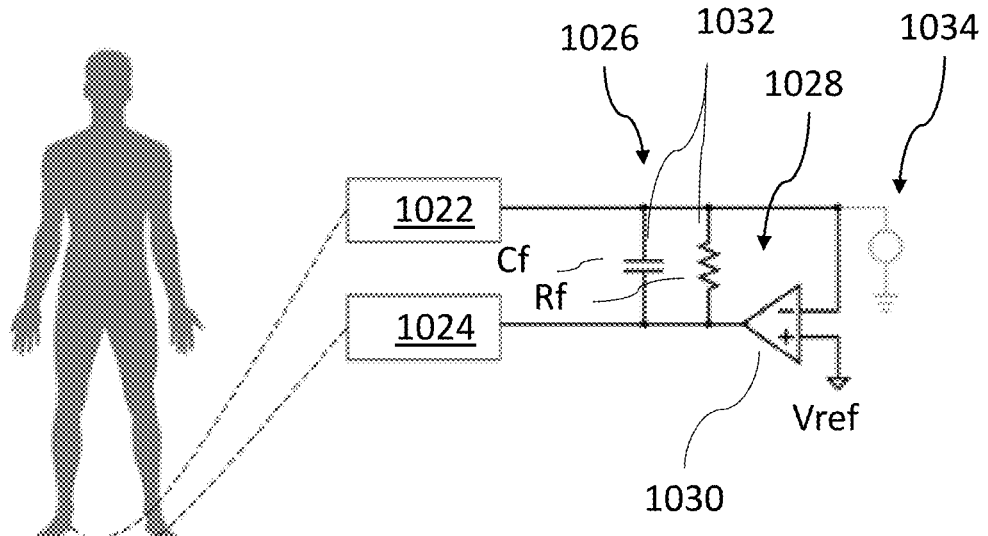
Figure 11:
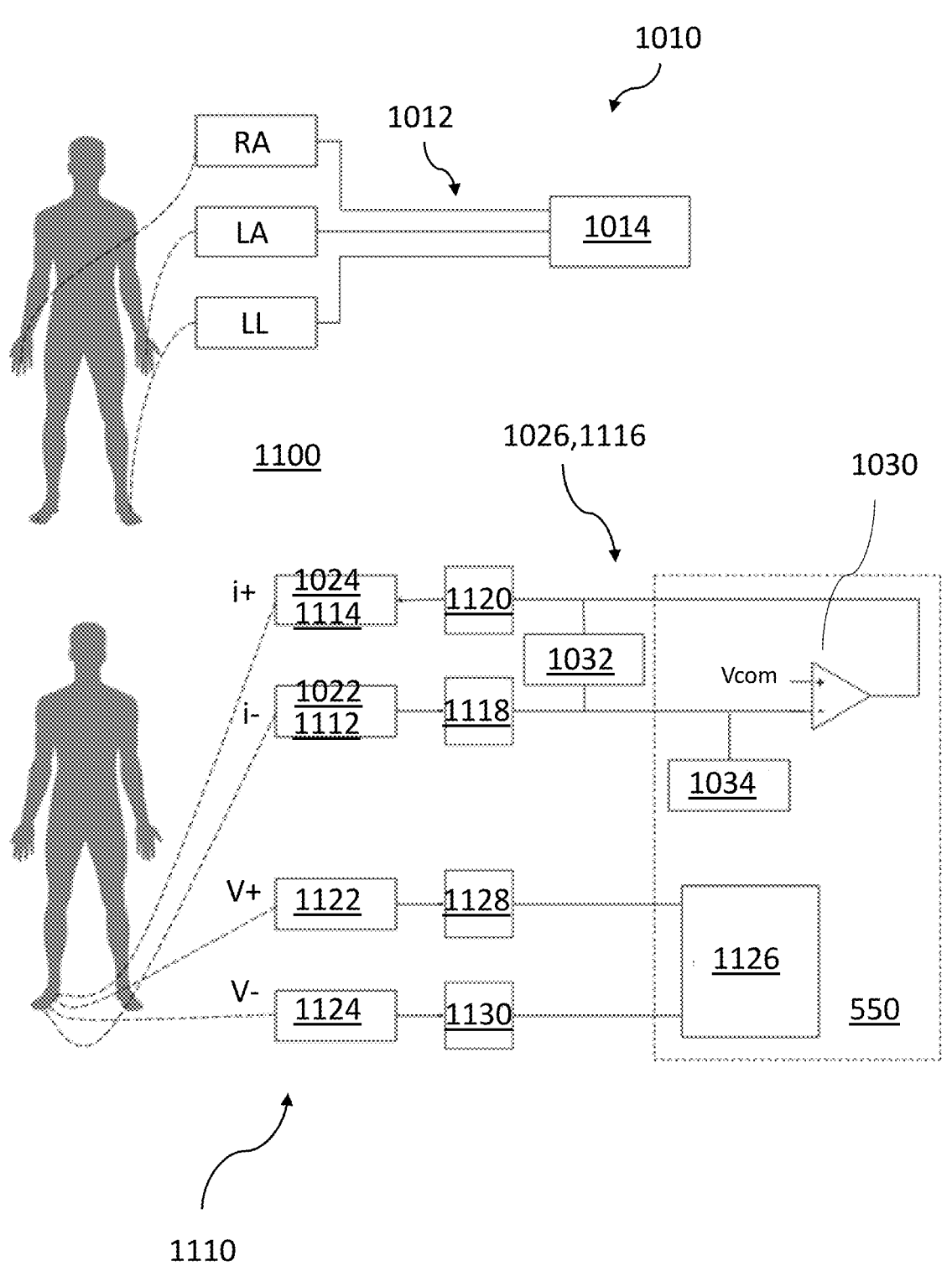
FIG. 11 illustrates a schematic view of an ECG acquisition system with a feedback device that is integrated with an impedance measurement system, according to an embodiment of the invention.

In an embodiment, the measurement station 100 includes an alternative to the RLD circuit that makes the acquisition of an ECG compatible with a simultaneous measurement that requires the injection of current into the human body (e.g., impedance measurement). FIG. 10 illustrates a configuration 1000 of an alternative arrangement to the RLD circuit (this is the same individual shown in duplicate for clarity) and FIG. 11 illustrates the integration of this configuration 1000 into a schematic 1100 that illustrates an ECG acquisition system 1010 and an impedance measurement system 1110.

The measurement station 100 includes an ECG acquisition system 1010. As previously indicated, this system includes a plurality of electrodes RA, LL, LL configured to contact different parts of a user's body. In particular, in the illustrated configuration, the plurality of electrodes includes the RA electrode mounted on the handle 110, the LA electrode mounted on the handle 110, and the LL electrode, mounted on the base 102. The electrodes RA, LA, LL are connected to an ECG electronic circuit 1012, which includes in particular an acquisition unit 1014 (AFE or control unit).

The measurement station 100 further includes two control electrodes 1022, 1024 configured to contact the user. These control electrodes 1022, 1024 may be on the base 102 of the measurement station 100. For example, the control electrodes 1022, 1024 are formed by electrically conductive paths 602 of the base 102. Both control electrodes 1022, 1024 may be part of the right group RG of electrodes of the base 102: the control electrode 1022 may comprise at least the R16 strip (R16 and R18 strip for example) and the control electrode 1024 may comprise at least the R4 strip (R2 and R4 strips for example). In the ECG acquisition system 1010, the LL electrode is taken from the electrodes of the left group LG of the base 102.

The control electrodes 1022, 1024 may be positioned anywhere on the body. Nevertheless, the choice of the base

102 for these two control electrodes 1022, 1024 has several benefits: the user is already in contact with the control electrodes 1022, 1024 when standing on the base 102 to perform an ECG (to be in contact with the LL electrode), and the control electrodes 1022, 1024 may also be used as current injection to perform, for example, an IPG. This will be explained in detail later.

The measurement station 100 further includes an electrical connection circuit 1026 that includes a feedback loop 1028 that connects the two control electrodes 1022, 1024.

One of the two control electrodes 1022, 1024 (control electrode 1022 in the 1000 configuration) is used to obtain the user's body potential. This potential is inverted and amplified by the feedback loop 1028 and then fed back to the body by the other of the two control electrodes 1022, 1024 (electrode 1024 in the 1000 configuration). In this way, the body potential is stabilized, and the ECG acquisition system is electrically stabilized.

In an embodiment, the feedback loop 1028 includes, in particular, an operational amplifier 1030 and a feedback connection 1032. The positive terminal of the operational amplifier 1030 is connected to a reference voltage Vref and the negative terminal of the operational amplifier 1030 is connected to the control electrode 1022. The output of the operational amplifier 1030 is connected to the control electrode 1024. The feedback connection 1032 connects the output of the operational amplifier 1030 to the negative input of the operational amplifier 1030.

The feedback connection 1028 includes at least one passive component (including a resistor, a capacitor, and/or an electromagnetic coil). For example, the at least one passive component may be a resistor Rf that forms the gain of the feedback loop 1028. The resistor Rf is selected with a high resistance value (e.g., about 10 MOhms). However, a high resistance Rf may cause difficulties in stabilizing the circuit diagram. To stabilize, the feedback connection 1032 may additionally include a capacitor Cf, in parallel with the resistor Rf. The value of the capacitor Cf may be about 47 pF.

In this particular configuration of the electrical connection circuit, the control electrode 1022 provides the potential of the user's body and the control electrode 1024 sets the user's body to a back-controlled potential.

The control electrodes 1022, 1024 are not part of the plurality of ECG electrodes (i.e. are distinct from them): they are independent (i.e. electrically independent) electrodes. Thus, configuration 1000 implements, for a multi-channel ECG, five independent electrodes: three electrodes RA, LL, LL for ECG acquisition and two control electrodes 1022, 1024 for controlling the body potential.

Furthermore, the electrical connection circuit 1026 is electrically independent of the ECG electronic circuit 1012. By electrically independent, it is meant that within the measurement station 100 there is no electrical connection between the electrical connection circuit 1026 and the ECG electronic circuit 1012. Common connections to the ground of the measurement station 100 are not considered as electrical connections. Similarly, a connection via the user's body is not considered an electrical connection.

As mentioned above, a benefit of the configuration 1000 of FIG. 10 is that it may allow, either simultaneously with the ECG or independently, a biophysical measurement involving the injection of current into the human body.

In an embodiment, the measurement station 100 includes an impedance measurement system 1110. The impedance measurement system includes a current source 1034 and two current injection electrodes 1112 (also noted as i−) and 1114

(also noted as i+) connected to the current source 1034 by a current injection circuit 1116.

In particular, the current injection circuit 1116 is the electrical connection circuit 1026 and the current injection electrodes 1112, 1114 are the control electrodes 1022, 1024.

Indeed, the linearity of the system allows the superposition of a stabilization circuit for the ECG and an impedance measurement system 1110. The connection circuit 1026 acts as a feedback loop for the current injection to control the current amplitude.

The current source 1034 may include a voltage generator connected to ground on the one hand and to the negative terminal of the operational amplifier 1030 via an RC circuit (series resistor and capacitor) on the other hand. The current source 1034 may be integrated with the AFE.

In an embodiment, the current source 1034 is an AC (alternative current) source (e.g., an AC voltage source in series with a capacitor and a resistor). A common-mode voltage may then exist. The feedback loop 1028, and in particular the feedback connection 1032, ensures that the operational amplifier 1030 operates within its range by allowing a loop for DC (direct current) current.

To prevent injection of low-frequency components or injection of DC current generated by the operational amplifier 1034, high-pass filters 1118, 1120 are positioned between the current injection electrodes 1112, 1114 and the current injection circuit 1116. The high pass filters 1118, 1120 may include capacitors and/or resistors. In an embodiment, the high-pass filter 1118 comprises a capacitor and the high-pass filter 1120 comprises a capacitor and a resistor in parallel. In another embodiment, the two high-pass filters 1118, 1120 each include a capacitor and a resistor in parallel.

The frequency of the injected alternating current may be between 5 kHz and 1000 kHz.

In order to activate the ECG acquisition system 1010 without activating the impedance measurement system 1110, the current source 1034 may be controllable (to be turned on or off), for example, via the AFE directly, or a switch may be positioned between the current source 1034 and the current injection circuit 1116, using, for example, the switch 566 and/or the control circuitry 550.

The impedance measurement system 1100 also includes two measurement electrodes 1122, 1124 (also noted as V+, V−, respectively) configured to measure a human body potential, and a voltmeter 1126, connected to the two measurement electrodes 1122, 1124.

To ensure that the voltmeter 1126 measures only high-frequency components, high-pass filters 1128, 1130 are positioned between the measurement electrodes 1122, 1124 and the voltmeter 1126. The high pass filters 1128, 1130 may include capacitors.

The measurement electrodes 1122, 1124 may be mounted on the base 102, and in particular in the same RG electrode group as the current injection electrodes 1112, 1114. In a configuration, the measurement electrodes 1122, 1124 are located between the current injection electrodes 1112, 1114. For example, conductive paths R14 and R6 may be used for the measurement electrodes 1122, 1124, respectively. The impedance measurement system 1110 allows for a so-called in-foot IPG: the impedance change of the foot may thus be measured.

Alternatively, by selecting an injection electrode 1112, 1114 and a measurement electrode 1122, 1124 in the left group of electrodes LG and an injection electrode 1112, 1114 and a measurement electrode 1122, 1124 in the right group of electrodes RG, the impedance measurement system 1100 allows to make a so-called "between legs" IPG: the impedance variation of the leg arch may thus be measured. For example, the conductive path L13 may form the current injection electrode 1112 (which is also the control electrode 1022), one or more of L1, L3, L5, L7 may form the measurement electrode 1124, one or more of R14, R16, R18 may form the current injection electrode 1114 (which is also the control electrode 1024), one or more of R2, R4, R6, R8 may form the measurement electrode 1122. One or more of conductive paths L15, L17 may form electrode LL. The electrodes RA and LA are on the handle 110.

More generally, instead of the impedance measurement system, the measurement station 100 may comprise a measurement system involving the injection of a current and/or the application of a voltage. The current source may be AC (IPG, BIA) and/or the voltage source may be DC (sweat activity measurement, described in WO2006/136598, WO2008/107324, WO2013/075963, WO2014/033105, WO2015/036530, WO2016/083432).

In an embodiment, an electrode of the ECG acquisition system is common with one of the control electrodes.

The acquisition of a synchronized ECG and IPG makes it possible to obtain, in particular, physiological data relating to the cardiovascular functioning of an individual (activation of the heart, blood flow in the limbs, etc.). The control circuitry 550 may drive the ECG acquisition system 1010 and the impedance measurement system 1110 in order to be able to: either launch an ECG alone, or launch an impedance measurement analysis alone (IPG, BIA, . . . ), or an ECG and an impedance measurement analysis simultaneously.

As noted above, the measurement station 100 further includes load cells capable of measuring a weight of the user. The load cells are also capable of performing a BCG (ballistocardiogram). Similarly, the monitoring circuitry 550 may perform a BCG, an ECG, and an IPG in a synchronized manner. The ECG may then be used to identify peaks in the BCG and IPG signals.

Figure 12:
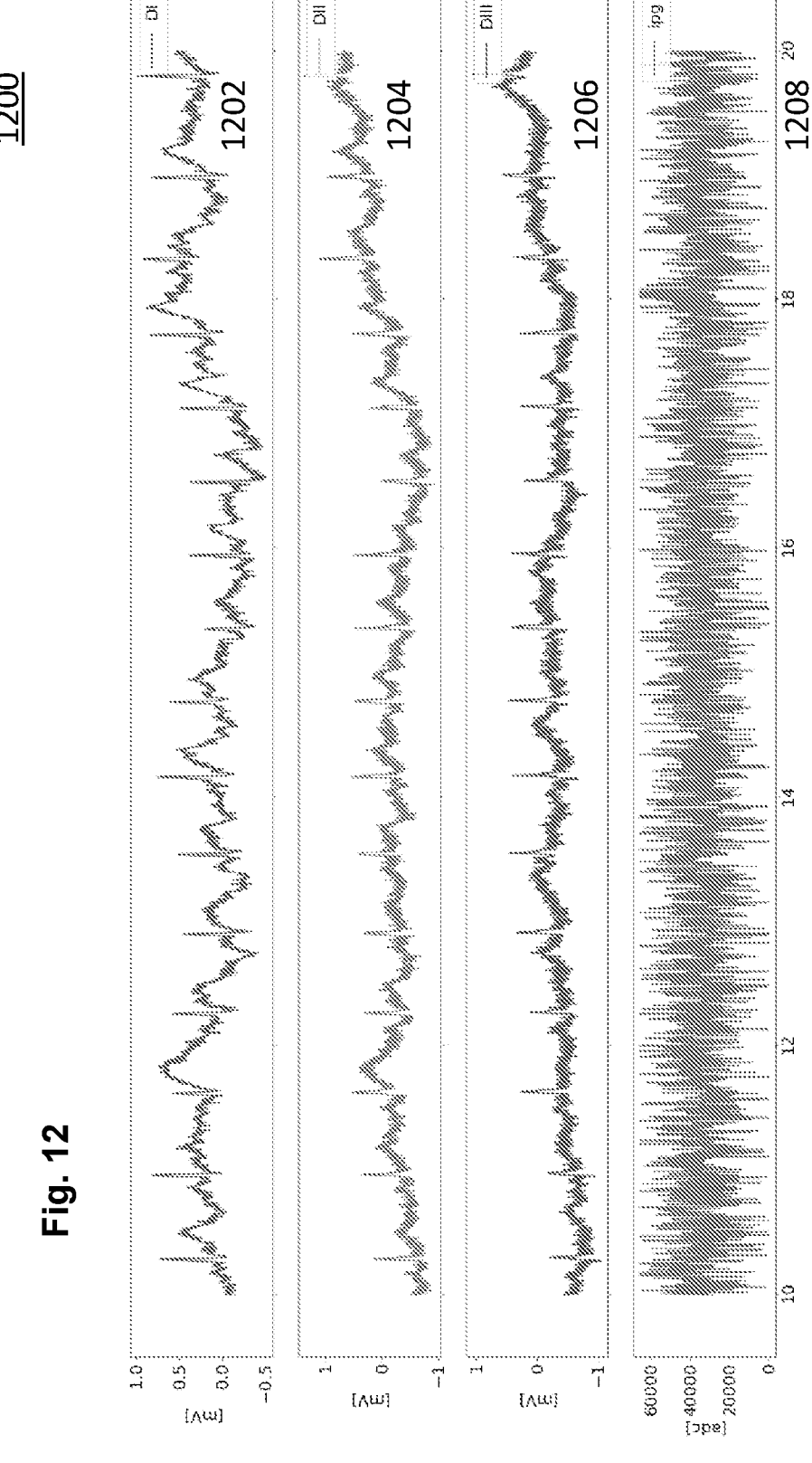
FIG. 12 shows measurements obtained with the scheme of FIG. 11, without IPG.

FIG. 12 shows ECG results 1200 with the configuration of FIG. 10 (without simultaneous acquisition of an IPG, therefore). The DI (between RA and LA) 1202, DII (between RA and LL) 1204, DIII (between LA and LL) 1206, and the IPG 1208 (in ADC steps) are shown synchronized. These signals are usable, with the obvious exception of the signal recovered for the IPG, since the current source 1034 was not activated. This FIG. 12 shows that the feedback loop defined by the two control electrodes 1022, 1024 allows to stabilize the ECG in order to obtain good quality signals.

Figure 13:
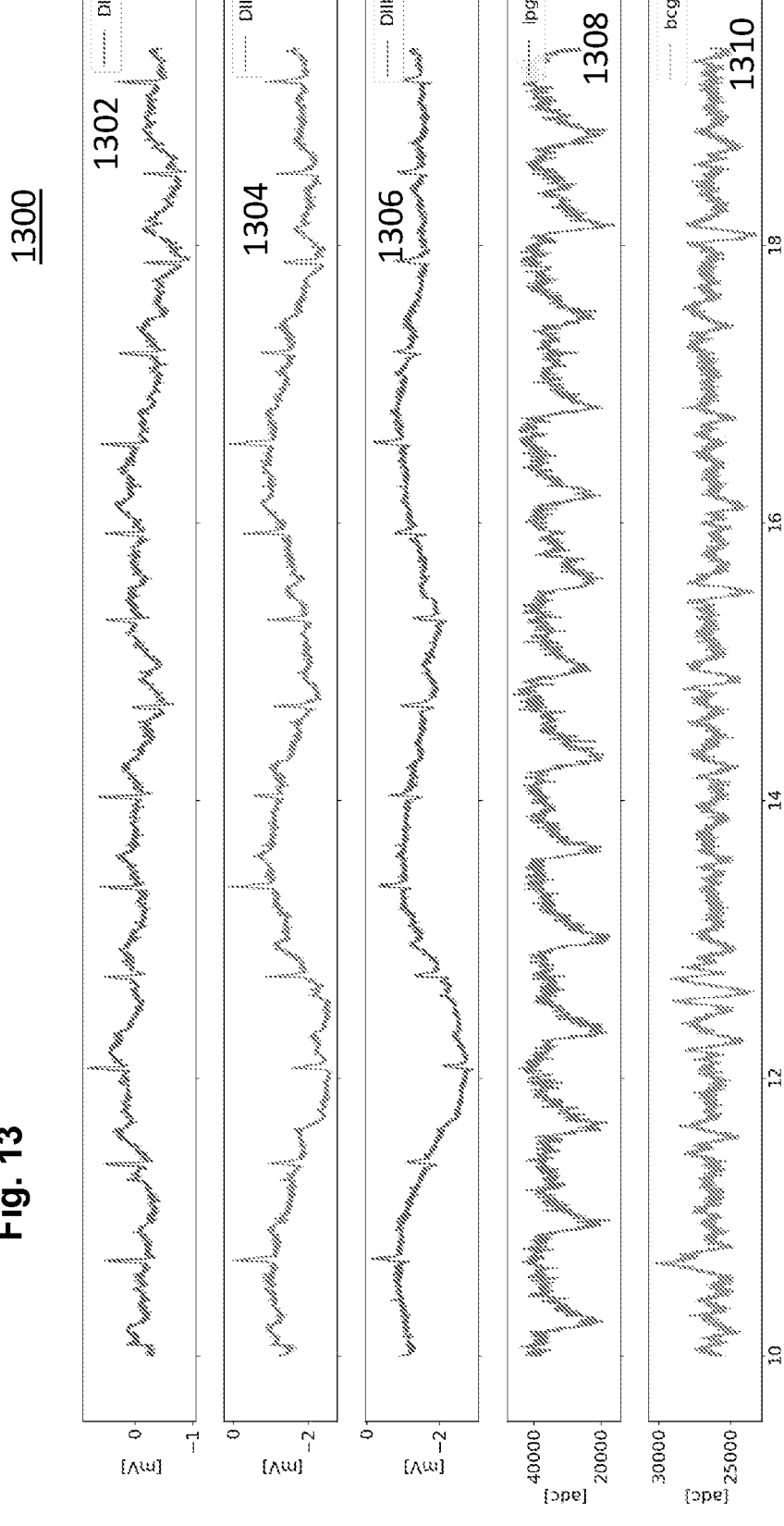
FIG. 13 shows measurements obtained with the scheme of FIG. 11, with IPG.

FIG. 13 shows results 1300 of an ECG performed with IPG simultaneously, with the configuration of FIG. 11. The DI lead (between RA and LA) 1302, DII lead (between RA and LL) 1304, DIII lead (between LA and LL) 1306, the IPG 1308 (in ADC steps), and a BCG 1310 (in ADC steps) are shown (synchronized). The measurements show that there is no saturation phenomenon, and the peaks are clearly identifiable. These signals are therefore usable. This FIG. 13 shows that an IPG and an ECG may be performed simultaneously. FIG. 13 also shows the BCG signal, acquired simultaneously.

The measurement station 100 may perform various measurements, such as BIA (between the legs or segmental with the handle). For this purpose, each conductive path 602 may be an electrode performing different functions. For this purpose, the measurement station 100 includes a switch for connecting the conductive paths 602 to different components.

In an example ("between legs" ECG and IPG), the strips L15 and L17 form the electrode (which is therefore be connected to the ECG electronic circuit 1012), the strip L13 forms the current injection electrode 1112 (which is therefore connected to the electrical connection circuit 1026), the strips L14, L16, L18 form the current injection electrode 1114 (which is therefore connected to the electrical connection circuit 1026), the strips L1, L3, L5, L7 form the measuring electrode 1124 (which is therefore be connected to the voltmeter 1126), the strips R2, R4, R6, R8 form the measuring electrode 1122 (which is therefore be connected to the voltmeter 1126).

In another example (ECG and IPG in the foot), strips L15 and L17 form the LL electrode (which is therefore connected to the ECG electronic circuit 1012), strips L16, L18 form the current injection electrode 1112 (which is therefore connected to the electrical connection circuit 1026), strips L2, L4 form the current injection electrode 1114 (which is therefore connected to the electrical connection circuit 1026), the L14 strip forms the measuring electrode 1124 (which is therefore connected to the voltmeter 1126), the L6 strip forms the measuring electrode 1122 (which is therefore be connected to the voltmeter 1126).

In particular, the switch 566 allows switching between these two configurations. In particular, it allows different electrodes to be connected to the electrical connection circuit 1026, depending on the desired measurement.

In addition, to perform a segmental BIA or to perform a left foot IPG, other configurations of the left LG and right RG electrode groups are possible, in which some electrodes are to be connected or disconnected from the electrical connection circuit 1026.

In an embodiment, the measurement station evaluates the sweat function of the skin (ESC measurement) by exciting the electrodes 602 with continuous and constant voltage steps. Patent applications WO2006/136598, WO2008/107324, WO2013/075963, WO2014/033105, WO2015/036530 WO2016/083432 explain this operation. In this embodiment, most of the electrodes 602 (all but one strip of each electrode group LG, RG, which may be connected to a high impedance), are connected to the DC voltage source.

Switch 566 allows one to switch between all these different configurations.

The measurement station 100 further includes load cells adapted to measure a weight of the user. The load cells are also capable of performing a BCG (ballistocardiogram). Similarly, the monitoring circuitry 550 may perform a BCG, an ECG, and an IPG in a synchronized manner. The ECG may then be used to identify peaks in the BCG and IPG.

In an embodiment, the measurement station 100 includes a user presence detection system (hereinafter referred to as "detection system"). In particular, this detection system detects that the user is in contact simultaneously with an electrode of the handle 110 (hereinafter referred to as "hand electrode") and with an electrode of the base 102 (hereinafter referred to as "foot electrode"). This may be referred to as "contact determination".

Such a system avoids launching measures that require the handle and that will necessarily be inconclusive.

The sensing system may generate data indicating that the contact is effective or that the contact is not effective. Alternatively, the sensing system does not generate data in the absence of contact with the foot and hand.

The detection system is part of the control circuitry 550 of the measurement station 100.

The sensing system may include electrodes (including the aforementioned foot electrode and hand electrode), a voltage generator (e.g., the voltage source 558), a voltmeter (e.g., the voltmeter 562), and a sensing circuit 574. In an embodiment, the foot electrode is set to a predetermined potential by the voltage generator (e.g., between 0.5V and 2V): if there is contact between the foot electrode and the body of the user, the body will be set to the predetermined potential. The voltmeter is used to measure the potential of the hand electrode: if there is contact between the hand electrode and the user's body, the hand electrode measures a potential close to the predetermined potential. For detection purposes, a predetermined threshold is selected; the predetermined threshold corresponds to the predetermined potential minus a deviation that may correspond to body potential losses. For example, if the predetermined potential is 2V, the threshold may be 1.5V.

In response to a measurement of a hand electrode potential above the threshold, the detection system indicates that the detection has occurred, and thus that the user is in position on the base 102 and holding the handle 110. The various measurements of the measurement station 100 that require the use of the handle may then be performed.

One or more measurement acquisition systems are defined by the handle, which correspond to measurement acquisition systems that require the handle: the ECG acquisition system is one of them, the impedance measurement system for segmental BIA is another.

The foot electrode and the hand electrode may be electrodes used by a handheld measurement acquisition system, such as an ECG acquisition system and/or an impedance measurement system.

In an embodiment, the handle measurement acquisition system is activated in response to a simultaneous contact detection by the detection system. In other words, the control circuitry 550, upon receiving a simultaneous contact detection by the measurement system, initiates measurements requiring the handle or interrupts the initiation of measurements requiring the handle.

The control circuitry 550, including the memory 526, may include a sequence of measurements to be performed by different measurement acquisition systems (weight, ECG, BIA, IPG, ESC, etc.). Some of these measurements require the handle. In response to a lack of simultaneous contact detection, the control circuitry may modify the sequence of measurements so that the measurements requiring the handle are not implemented. Additionally or alternatively, in response to a detection of simultaneous contact, the control circuitry may modify the sequence of measurements so that measurements requiring the handle are implemented.

In a sequence of successive measurements M1, M2, M3, M4, where M2 requires the handle 110, the control circuitry 550 may generate the sequence M1, M3, M4 in response to a lack of simultaneous contact detection.

For example, the ECG acquisition system may be implemented in response to a simultaneous contact detection by the sensing system.

The user may voluntarily decide not to grasp the handle: thanks to the detection system, the measurement sequence may be significantly shorter since the measurements using the handle may be removed from the sequence In an embodiment, the base 102 includes a weight measurement system (e.g., with a weight sensor as described above). The detection system may be activated in response to a weight detection by the weight measurement system. This therefore allows the detection system to be activated only when a user is present on the scale, in order to save the battery of the measurement station 100. In particular, the measurement sequence may be triggered by the detection of weight by the weight measurement system (the first measurement may be the measurement of weight itself).

In an embodiment, the control circuitry 550 (and in particular the memory) stores a full measurement sequence, which includes all measurements permitted by the measurement station 100, including measurements requiring the handle 110, and stores a partial measurement sequence, which includes at most all measurements not requiring the handle 110. In particular, the control circuitry may switch from one full sequence to one partial sequence to the other based on no simultaneous contact detection by the detection system or, conversely the control circuitry may switch from one partial sequence to one full sequence to the other based on simultaneous contact detection. The switchover may also occur between two measurements requiring the handle, if the user releases the handle.

The control circuitry 550 may implement, by executing instructions of a computer program, different measurement methods. The instruction are stored in a memory and executed by a processor of the control circuitry to carry out the different measurement methods.

Figure 14:
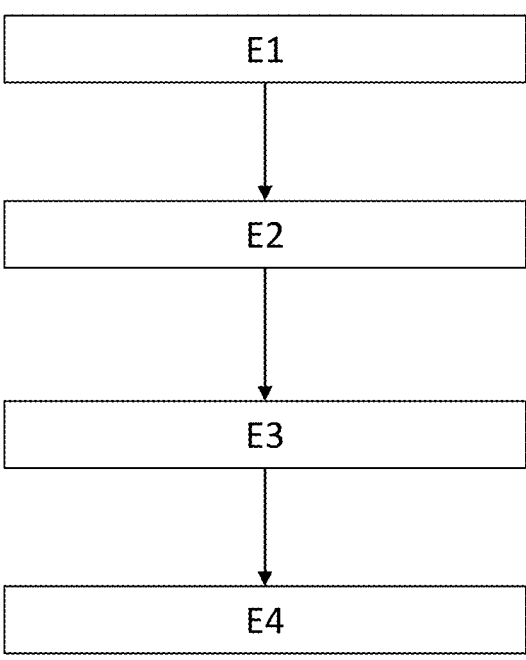
FIG. 14 illustrates an ECG acquisition process.

In an ECG method illustrated in FIG. 14, the control circuitry 550 may implement the following steps:

E1: connecting the control electrodes 1022, 1024 to the electrical connection circuit 1028, via switch 566, E2: if necessary, deactivating the current source 1034 or disconnecting the current source 1034 from the electrical connection circuit 1028, E3: activating of the ECG 1010 acquisition system to acquire an ECG, E4: ECG analyzing and processing.

Step E4 may include: heart rate calculating, anomaly identifying.

Figure 15:
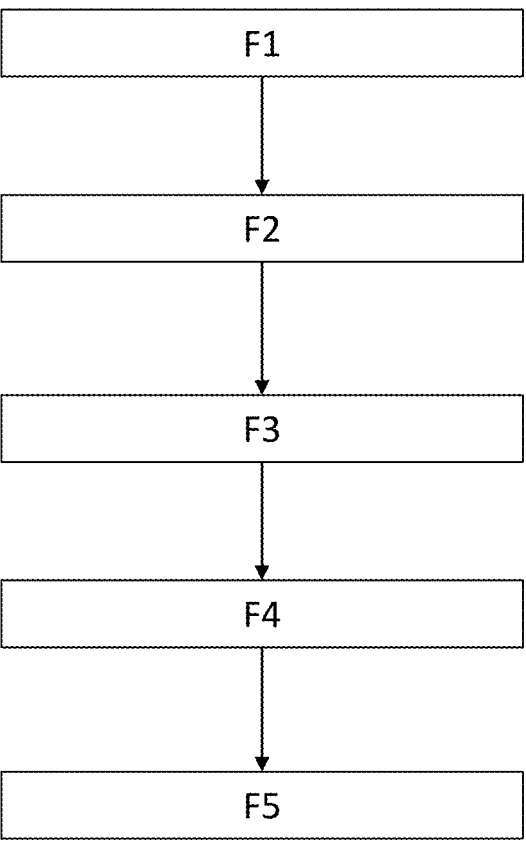
FIG. 15 illustrates a method for synchronized acquisition of ECG and IPG.

In an ECG and impedance measurement (e.g., IPG) method, shown in FIG. 15, the control circuitry 550 may implement the following steps:

F1: connecting the control electrodes 1022, 1024 to the electrical connection circuit 1028, via switch 566, F2: connecting the measuring electrodes 1122, 1124 to the voltmeter 1126 via the switch (the current injection electrodes 1114, 1112 being already connected to the current source via the electrical connection circuit 1026), F3: simultaneously activating the ECG acquisition system 1010 and the impedance measurement system 1110 (and in particular of the current source 1034 to inject a current into the user's body) to acquire an ECG and an impedance measurement (for example an IPG), F4: analyzing and processing the ECG and impedance measurement (e.g. IPG).

Step F4 may comprise the same calculations as step E4, with may further include determining information relating to PWV (pulse wave velocity), or blood pressure, or/and PAT (pulse arrival time). These additional measurements are enabled by the addition of a simultaneous impedance measurement (an IPG in this case). Step E3 and/or step F3 may also include the acquisition of an IPG in a synchronized manner. The control circuitry 550 may control the acquisition of a BCG, using the load cells of the base 102. The measurement station 100 may then obtain an ECG, an IPG and a BCG that are synchronized.

It will be appreciated that the various embodiments described previously are combinable according to any technically permissible combinations.

The invention claimed is:

1. A measurement station comprising:
an electrocardiogram (ECG) acquisition system,
two control electrodes configured to contact a user, an electrical connection circuit, the electrical connection circuit comprising a feedback loop connected to each of the two control electrodes,
an impedance measurement system,
wherein:
(i) the ECG acquisition system comprises:
a plurality of ECG electrodes configured to contact a user's body,
an ECG electronic circuit connected to the plurality of ECG electrodes, and wherein the two control electrodes are distinct from the plurality of ECG electrodes such that neither of the two control electrodes is used by the ECG acquisition system to collect ECG signals,
(ii) the impedance measurement system comprises:
a current source,
two current injection electrodes adapted to inject a current into a user's body, and wherein the current source is connected to the electrical connection circuit and the two current injection electrodes are the two control electrodes, and
(iii) the electrical connection circuit is electrically independent of the ECG electronic circuit.

2. The measurement station according to claim 1, wherein:
one of the two control electrodes is configured to measure a potential of a user body to obtain a measured potential,
the feedback loop is configured to amplify and invert the measured potential to obtain an amplified and inverted potential, and
the other of the two control electrodes is configured to set the user's body to the amplified and inverted potential.

3. The measurement station according to claim 1, wherein the feedback loop comprises:
an operational amplifier, and
a feedback connection connecting an output of the operational amplifier to an input of the operational amplifier, the feedback connection comprising at least one passive component.

4. The measurement station according to claim 3, wherein the passive component comprises a resistor and/or a capacitor.

5. The measurement station according to claim 3, wherein the control electrodes are connected to the input and output of the operational amplifier respectively.

6. The measurement station according to claim 1 wherein the current source is an alternative current source.

7. The measurement station according to claim 1 comprising a switch adapted to disconnect the electrical connection circuit and the current source, or wherein the current source is adapted to be deactivated.

8. The measurement station according to claim 1 wherein the impedance measurement system comprises two measuring electrodes adapted to measure a potential difference of a portion of the user's body crossed by a current generated by the current source.

9. The measurement station according to claim 1 wherein the ECG acquisition system and the impedance measurement system are configured to be activated simultaneously to acquire a synchronized ECG and impedance measurement.

10. The measurement station according to claim 1, comprising a base adapted to receive feet of a user and on which is mounted at least one of the two control electrodes.

11. The measurement station according to claim 1, wherein:

the two control electrodes are mounted on the base,
two ECG electrodes of the plurality of ECG electrodes are mounted on the handle, and
an ECG electrode of the plurality of ECG electrodes is mounted on the base.

12. A method of acquiring an electrocardiogram, ECG, using a measurement station according to claim 1, comprising:
connecting the control electrodes to the electrical connection circuit via a switch, and
activating the ECG acquisition system to acquire an ECG.

13. The method according to claim 12, comprising, before activating the ECG acquisition system:
deactivation of the current source or disconnection of the current source from the electrical connection circuit.

14. A method of acquiring an electrocardiogram, ECG, and an impedance measurement using a measurement station according to claim 7, the method comprising:
connecting the control electrodes to the electrical connection circuit via the switch, and
simultaneously activating the control electrodes to the electrical connection circuit via the switch, and simultaneously activating the ECG acquisition system and the impedance measurement system to acquire an ECG and an impedance measurement.

15. The method according to claim 14, wherein the impedance measurement is an impedance plethysmogram (IPG).

16. The measurement station according to claim 1, further comprising a base adapted to receive a user's feet and on which is mounted at least one of the two control electrodes.

17. The measurement station according to claim 16, wherein the base comprises a weight measurement system including a weight sensor and the measurement station is configured to activate a detection system in response to a weight detection by the weight measurement system.

18. The measurement station according to claim 1, wherein the feedback loop comprises an operational amplifier, the operational amplifier having a first input coupled to a reference voltage, a second input coupled to a first one of the two control electrodes, and an output coupled to a second one of the two control electrodes.

19. The measurement station according to claim 1, wherein the feedback loop is configured to amplify and invert a potential measured at one of the control electrodes and to apply a corresponding drive signal to the other control electrode so as to stabilize a body potential during ECG acquisition.

20. The measurement station of claim 1, wherein the electrical connection circuit is configured to provide a DC return path through the feedback loop to maintain the operational amplifier within its operating range when an AC current is injected by an impedance measurement system.

21. The measurement station of claim 1, wherein the feedback loop is configured to control a common-mode body potential during simultaneous acquisition of ECG and impedance measurements so as to reduce saturation and interference between the two acquisitions.

22. The measurement station of claim 1, wherein the feedback loop is configured to generate, responsive to a signal obtained via a first of the two control electrodes, a drive signal to be applied via a second of the two control electrodes to set a potential of the user's body.

\* \* \* \* \*